United States Patent
Cox et al.

(10) Patent No.: US 12,246,326 B2
(45) Date of Patent: Mar. 11, 2025

(54) SYSTEMS AND APPARATUS FOR HOLDING PLATES

(71) Applicant: 10X Genomics, Inc., Pleasanton, CA (US)

(72) Inventors: David Maurice Cox, Pleasanton, CA (US); Stefanie Nishimura, Pleasanton, CA (US); Lauren Wong, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 99 days.

(21) Appl. No.: 17/009,219

(22) Filed: Sep. 1, 2020

(65) Prior Publication Data

US 2020/0391215 A1    Dec. 17, 2020

Related U.S. Application Data

(63) Continuation of application No. PCT/US2019/020425, filed on Mar. 1, 2019.

(60) Provisional application No. 62/702,702, filed on Jul. 24, 2018, provisional application No. 62/638,036, filed on Mar. 2, 2018.

(51) Int. Cl.
B01L 9/00 (2006.01)

(52) U.S. Cl.
CPC ......... *B01L 9/523* (2013.01); *B01L 2200/025* (2013.01)

(58) Field of Classification Search
CPC ................. B01L 9/523; B01L 2200/02; B01L 2200/025; B01L 2300/0829
See application file for complete search history.

(56) References Cited

U.S. PATENT DOCUMENTS

| | | |
|---|---|---|
| 5,658,548 A | 8/1997 | Padhye et al. |
| 5,705,628 A | 1/1998 | Hawkins |
| 5,897,783 A | 4/1999 | Howe et al. |
| 6,133,436 A | 10/2000 | Koster et al. |
| 7,718,421 B2 | 5/2010 | Chen et al. |
| 9,347,056 B2 | 5/2016 | Saito et al. |
| 9,975,122 B2 | 5/2018 | Masquelier et al. |
| 10,245,587 B2 | 4/2019 | Masquelier et al. |
| 10,544,413 B2 | 1/2020 | Bharadwaj et al. |
| 10,697,000 B2 | 6/2020 | Belgrader et al. |
| 11,135,584 B2 | 10/2021 | Masquelier et al. |
| 2002/0174878 A1 | 11/2002 | Nisson et al. |

(Continued)

FOREIGN PATENT DOCUMENTS

| | | |
|---|---|---|
| EP | 1348966 A2 | 10/2003 |
| EP | 1944368 A1 | 7/2008 |

(Continued)

OTHER PUBLICATIONS

U.S. Appl. No. 17/471,603, filed Mar. 31, 2022, Masquelier et al.

(Continued)

*Primary Examiner* — Elizabeth A Robinson
*Assistant Examiner* — Austin Q Le
(74) *Attorney, Agent, or Firm* — Clark & Elbing LLP

(57) ABSTRACT

Provided herein are devices and methods for securing microplates and/or microplates comprising tube strips. The devices provided herein may use a magnetic force to secure the microplates and/or the tube strips during heat sealing of wells or tubes.

22 Claims, 8 Drawing Sheets

(56) References Cited

U.S. PATENT DOCUMENTS

| | | |
|---|---|---|
| 2003/0027203 A1 | 2/2003 | Fields |
| 2004/0040851 A1 | 3/2004 | Karger et al. |
| 2004/0165332 A1* | 8/2004 | Beson .................. B44B 5/02 |
| | | 361/144 |
| 2004/0214175 A9 | 10/2004 | McKernan et al. |
| 2004/0228763 A1 | 11/2004 | Ingenhoven et al. |
| 2005/0013741 A1 | 1/2005 | a' Brassard |
| 2005/0025673 A1* | 2/2005 | Shimei .................. B01L 9/543 |
| | | 422/400 |
| 2006/0094108 A1 | 5/2006 | Yoder et al. |
| 2007/0065808 A1 | 3/2007 | Bohm et al. |
| 2007/0117086 A1 | 5/2007 | Evans et al. |
| 2007/0251341 A1 | 11/2007 | Balmer |
| 2008/0003142 A1 | 1/2008 | Link et al. |
| 2008/0053205 A1 | 3/2008 | Pollack et al. |
| 2009/0305397 A1 | 12/2009 | Dodgson et al. |
| 2010/0006441 A1 | 1/2010 | Renaud et al. |
| 2011/0005978 A1 | 1/2011 | Bohm et al. |
| 2011/0114490 A1 | 5/2011 | Pamula et al. |
| 2011/0177592 A1 | 7/2011 | Faustman et al. |
| 2012/0015382 A1 | 1/2012 | Weitz et al. |
| 2012/0122714 A1 | 5/2012 | Samuels et al. |
| 2012/0190037 A1 | 7/2012 | Durin et al. |
| 2012/0196288 A1 | 8/2012 | Beer |
| 2013/0074944 A1 | 3/2013 | Van Gelder |
| 2013/0315800 A1* | 11/2013 | Yin .................. G01N 35/0098 |
| | | 422/561 |
| 2013/0323741 A1 | 12/2013 | Bernet et al. |
| 2014/0235506 A1 | 8/2014 | Hindson et al. |
| 2015/0031037 A1 | 1/2015 | Li et al. |
| 2015/0336096 A1 | 11/2015 | Smith et al. |
| 2015/0361418 A1 | 12/2015 | Reed |
| 2016/0298107 A1 | 10/2016 | O'Farrell et al. |
| 2017/0336306 A1 | 11/2017 | Miller et al. |
| 2018/0071741 A1* | 3/2018 | Kelly ............ G01N 35/00029 |
| 2018/0147574 A1* | 5/2018 | Dysli .................. G01N 35/028 |
| 2018/0362963 A1 | 12/2018 | Stelling |
| 2019/0039034 A1 | 2/2019 | Siow et al. |
| 2019/0234977 A1* | 8/2019 | Antinjuntti ............ G01N 35/02 |
| 2019/0329245 A1 | 10/2019 | Masquelier et al. |
| 2020/0115703 A1 | 4/2020 | Bharadwaj et al. |
| 2021/0032678 A1 | 2/2021 | Belgrader et al. |
| 2021/0187515 A1 | 6/2021 | Alimsijah et al. |
| 2021/0293693 A1 | 9/2021 | Bharadwaj et al. |
| 2022/0097045 A1 | 3/2022 | Masquelier et al. |
| 2022/0268795 A1 | 8/2022 | Alimsijah et al. |

FOREIGN PATENT DOCUMENTS

| | | |
|---|---|---|
| EP | 3262407 A1 | 1/2018 |
| EP | 3517974 A1 | 7/2019 |
| EP | 3605109 A1 | 2/2020 |
| WO | WO-2006/071770 A2 | 7/2006 |
| WO | WO-2007/140015 A2 | 12/2007 |
| WO | WO-2010/009365 A1 | 1/2010 |
| WO | WO-2011/059443 A1 | 5/2011 |
| WO | WO-2012/019765 A1 | 2/2012 |
| WO | WO-2012/156744 A2 | 11/2012 |
| WO | WO-2014/182835 A1 | 11/2014 |
| WO | WO-2014/210353 A2 | 12/2014 |
| WO | WO-2015/200717 A2 | 12/2015 |
| WO | WO-2016/137973 A1 | 9/2016 |
| WO | WO-2016/193758 A1 | 12/2016 |
| WO | WO-2018/213643 A1 | 11/2018 |
| WO | WO-2019/169347 A1 | 9/2019 |
| WO | WO-2020/123657 A2 | 6/2020 |

OTHER PUBLICATIONS

International Search Report and Written Opinion for PCT Application No. PCT/US2019/020425, mailed May 13, 2019 (13 pages).
U.S. Appl. No. 17/242,802, Salmanzadeh.
U.S. Appl. No. 17/314,756, Salmanzadeh.
U.S. Appl. No. 17/332,371, Salmanzadeh et al.
U.S. Appl. No. 17/338,215, Salmanzadeh et al.
U.S. Appl. No. 17/587,861, Shah.
U.S. Appl. No. 17/851,416, Bharadwaj et al.
Anonymous: "Dynal MPC(TM)-S", Oct. 13, 2008 (Oct. 13, 2008), XP055603532, Retrieved from the Internet on Jul. 9, 2019; URL:<https://www.veritastk.co.jp/products/pdf/120%2020D.Dynal_MPC-S%28rev005%29.pdf>.
Beneyton et al., "High-throughput screening of filamentous fungi using nanoliter-range droplet-based microfluidics," Sci Rep. 6:27223 (Jun. 2016) (10 pages).
Brouzes et al., "Rapid and continuous magnetic separation in droplet microfluidic devices," available in PMC Feb. 7, 2016, published in final edited form as: Lab Chip. 15(3):908-919 (2015) (23 pages).
Chokkalingam et al., "Probing cellular heterogeneity in cytokine-secreting immune cells using droplet-based microfluidics," Lab Chip. 13(24): 4740-4744 (2013).
Hu et al., "Efficient cell pairing in droplets using dual-color sorting," Lab Chip. 15(20):3989-93 (2015).
Jo et al., "Magnetophoretic sorting of single cell-containing microdroplets," Micromachines (Basel). 7(4): 56 (2016) (9 pages).
Klein et al., "Droplet barcoding for single-cell transcriptomics applied to embryonic stem cells," Cell. 161(5): 1187-1201 (2015) (May 21, 2015) (22 pages).
Lagus et al., "A review of the theory, methods and recent applications of high-throughput single-cell droplet microfluidics," Journal of Physics D: Applied Physics. 46:114005 (2013) (21 pages).
Lennon et al., "A scalable, fully automated process for construction of sequence-ready barcoded libraries for 454," Genome Biol. 11(2):R15 (2010) (9 pages).
Shembekar et al., "Droplet-based microfluidics in drug discovery, transcriptomics and high-throughput molecular genetics," Lab Chip. 16(8):1314-31 (Mar. 2016).

\* cited by examiner

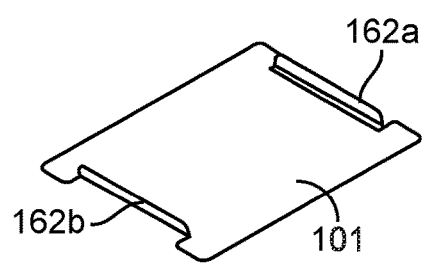
FIG. 7A
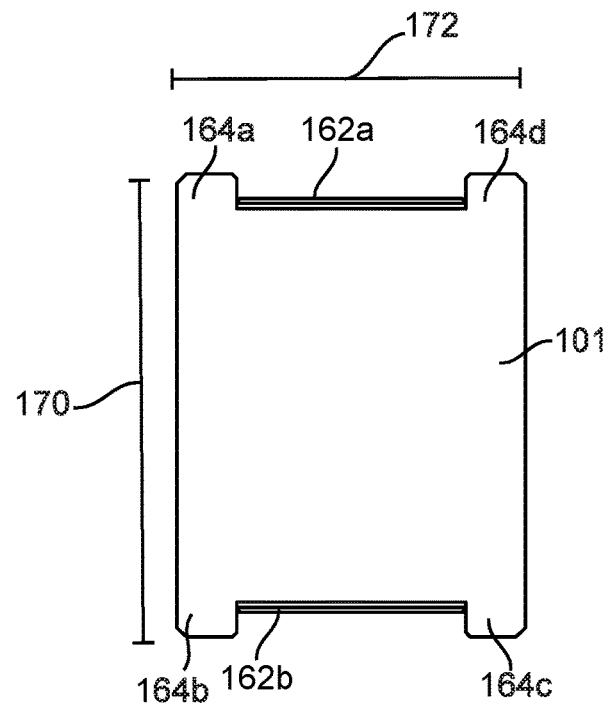
FIG. 7B
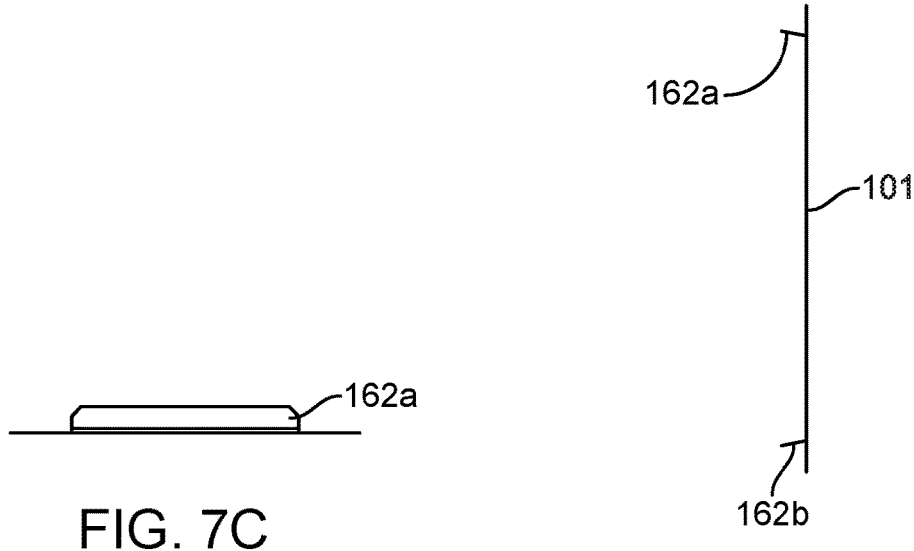
FIG. 7C
FIG. 7D

SYSTEMS AND APPARATUS FOR HOLDING PLATES

CROSS-REFERENCE

This application claims priority to U.S. Provisional Patent Application No. 62/638,036 filed Mar. 2, 2018, and U.S. Provisional Patent Application No. 62/702,702 filed Jul. 24, 2018, which applications are herein incorporated by reference in their entirety for all purposes.

BACKGROUND

Whole genome sequencing (WGS) has been a valuable research tool, and is currently being introduced in the clinical setting for the detection and monitoring of diseases. In WGS, thermal cycling is often used to amplify nucleic acids by performing polymerase chain reactions (PCR), for example, and other reactions. PCR is typically carried out in containers such as tubes, plates, or trays having multiple wells. In such containers, reagents such as DNA polymerase, nucleotides, oligonucleotide primers, buffers, and a DNA template are exposed to thermal cycling to promote amplification of the DNA template. The wells in PCR plates are typically sealed during the PCR cycling to minimize volume loss and contamination of material contained within. Heat-sealed cover sheets, adhesive cover sheets, caps, or other such sealing means are often used to seal the wells in the PCR plates (i.e., microplates).

SUMMARY

In an aspect, the present disclosure provides a microplate holder for securing a microplate, said microplate holder comprising: a base plate; an aligner configured to accept said microplate, wherein said aligner comprises a proximal surface, a distal surface, and an attraction unit between said proximal surface and said distal surface, which attraction unit is attractable towards said base plate to position said aligner adjacent to said base plate; and a frame configured to rest adjacent to said aligner and a proximal surface of said microplate, wherein said frame comprises a plurality of projections that extend along a direction parallel to said proximal surface of said aligner when said frame is positioned adjacent to said aligner.

In some embodiments, the base plate comprises an additional attraction unit. In some embodiments, the additional attraction unit is a magnet. In some embodiments, the magnet is a permanent magnet. In some embodiments, the magnet is an electromagnet. In some embodiments, the magnet comprises a ferromagnetic material. In some embodiments, the ferromagnetic material is copper, iron, ferric oxide, iron (II, III) oxide, manganese, nickel, yttrium iron garnet, chromium dioxide, gadolinium, terbium, dysprosium, trevorite, europium oxide, or a combination thereof. In some embodiments, the base plate comprises one or more posts that are attractable towards said attraction unit. In some embodiments, the one or more posts comprises an additional attraction unit. In some embodiments, the additional attraction unit is a magnet. In some embodiments, the magnet is a permanent magnet. In some embodiments, the magnet is an electromagnet. In some embodiments, the magnet comprises a ferromagnetic material. In some embodiments, the ferromagnetic material is copper, iron, ferric oxide, iron (II, III) oxide, manganese, nickel, yttrium iron garnet, chromium dioxide, gadolinium, terbium, dysprosium, trevorite, europium oxide, or a combination thereof.

In some embodiments, the additional attraction unit comprises an electrode that supplies an electric field from said electrode to said aligner, or vice versa. In some embodiments, the one or more posts are configured to abut at least one edge of said microplate. In some embodiments, the one or more posts restrict a lateral or longitudinal movement of said microplate. In some embodiments, the base plate comprises a first tab extending from a first longitudinal side of said base plate and a second tab extending from a second longitudinal side of said base plate. In some embodiments, the first tab and said second tab are configured to engage a first longitudinal side of said microplate and a second longitudinal side of said microplate.

In some embodiments, the aligner further comprises a first arm extending from a first end of said lateral wall and a second arm extending from a second end of said lateral wall. In some embodiments, the first arm surrounds a first corner of said microplate and said second arm surrounds a second corner of said microplate. In some embodiments, the frame is configured to be reversibly attached to said aligner. In some embodiments, the frame comprises at least one frame hole configured to align with at least one aligner hole. In some embodiments, the at least one frame hole and said at least one aligner hole are configured to accept a screw or a securing pin. In some embodiments, the screw or said securing pin anchors said frame and said aligner together. In some embodiments, the frame comprises one or more snapping tabs extending from a side of said frame. In some embodiments, the one or more snapping tabs makes a mechanical contact with one or more aligner snapping tab apertures.

In some embodiments, the frame comprises an additional attraction unit. In some embodiments, the additional attraction unit is a magnet. In some embodiments, the magnet is a permanent magnet. In some embodiments, the magnet is an electromagnet. In some embodiments, the magnet comprises a ferromagnetic material. In some embodiments, the ferromagnetic material is copper, iron, ferric oxide, iron (II, III) oxide, manganese, nickel, yttrium iron garnet, chromium dioxide, gadolinium, terbium, dysprosium, trevorite, europium oxide, or a combination thereof. In some embodiments, the additional attraction unit comprises an electrode that supplies an electric field from said electrode to said base plate, or vice versa. In some embodiments, the additional attraction unit is attractable towards said aligner to position said frame adjacent to said aligner and said proximal surface of said microplate. In some embodiments, the microplate holder prevents or restricts movement of said microplate. In some embodiments, the movement is a lateral movement, a longitudinal movement, or a proximal movement away from said base plate.

In another aspect, the present disclosure provides a method of securing a microplate, comprising: attaching a microplate holder to the microplate, said microplate holder comprising: a base plate; an aligner configured to accept said microplate, wherein said aligner comprises a proximal surface, a distal surface, and an attraction unit between said proximal surface and said distal surface, which attraction unit is attractable towards said base plate to position said aligner adjacent to said base plate; and a frame configured to rest adjacent to said aligner and a proximal surface of said microplate, wherein said frame comprises a plurality of projections that extend along a direction parallel to said proximal surface of said aligner when said frame is positioned adjacent to said aligner.

In some embodiments, the base plate comprises an additional attraction unit. In some embodiments, the additional attraction unit is a magnet. In some embodiments, the magnet is a permanent magnet. In some embodiments, the magnet is an electromagnet. In some embodiments, the magnet comprises a ferromagnetic material. In some embodiments, the ferromagnetic material is copper, iron, ferric oxide, iron (II, III) oxide, manganese, nickel, yttrium iron garnet, chromium dioxide, gadolinium, terbium, dysprosium, trevorite, europium oxide, or a combination thereof. In some embodiments, the base plate comprises one or more posts that are attractable towards said attraction unit. In some embodiments, the one or more posts comprises an additional attraction unit. In some embodiments, the additional attraction unit is a magnet. In some embodiments, the magnet is a permanent magnet. In some embodiments, the magnet is an electromagnet. In some embodiments, the magnet comprises a ferromagnetic material. In some embodiments, the ferromagnetic material is copper, iron, ferric oxide, iron (II, III) oxide, manganese, nickel, yttrium iron garnet, chromium dioxide, gadolinium, terbium, dysprosium, trevorite, europium oxide, or a combination thereof.

In some embodiments, the additional attraction unit comprises an electrode that supplies an electric field from said electrode to said aligner, or vice versa. In some embodiments, the one or more posts are configured to abut at least one edge of said microplate. In some embodiments, the one or more posts restrict a lateral or longitudinal movement of said microplate. In some embodiments, the base plate comprises a first tab extending from a first longitudinal side of said base plate and a second tab extending from a second longitudinal side of said base plate. In some embodiments, the first tab and said second tab are configured to engage a first longitudinal side of said microplate and a second longitudinal side of said microplate.

In some embodiments, the aligner further comprises a first arm extending from a first end of said lateral wall and a second arm extending from a second end of said lateral wall. In some embodiments, the first arm surrounds a first corner of said microplate and said second arm surrounds a second corner of said microplate. In some embodiments, the frame is configured to be reversibly attached to said aligner. In some embodiments, the frame comprises at least one frame hole configured to align with at least one aligner hole. In some embodiments, the at least one frame hole and said at least one aligner hole are configured to accept a screw or a securing pin. In some embodiments, the screw or said securing pin anchors said frame and said aligner together. In some embodiments, the frame comprises one or more snapping tabs extending from a side of said frame. In some embodiments, the one or more snapping tabs makes a mechanical contact with one or more aligner snapping tab apertures.

In some embodiments, the frame comprises an additional attraction unit. In some embodiments, the additional attraction unit is a magnet. In some embodiments, the magnet is a permanent magnet. In some embodiments, the magnet is an electromagnet. In some embodiments, the magnet comprises a ferromagnetic material. In some embodiments, the ferromagnetic material is copper, iron, ferric oxide, iron (II, III) oxide, manganese, nickel, yttrium iron garnet, chromium dioxide, gadolinium, terbium, dysprosium, trevorite, europium oxide, or a combination thereof. In some embodiments, the additional attraction unit comprises an electrode that supplies an electric field from said electrode to said base plate, or vice versa. In some embodiments, the additional attraction unit is attractable towards said aligner to position said frame adjacent to said aligner and said proximal surface of said microplate. In some embodiments, the microplate holder prevents or restricts movement of said microplate. In some embodiments, the movement is a lateral movement, a longitudinal movement, or a proximal movement away from said base plate.

Current methods of heat sealing wells in microplates often lead to warping or deformation of test tubes or other plastic material of the microplates due to a lack of stabilization of the microplates during the heat sealing process. The warpage or dimensional deformation of the tubes and/or the wells leads to inefficient sealing that in turn, leads to an evaporation of a reagent volume. The present disclosure provides devices and methods that may be useful in preventing warping of plastic tubes and/or wells of microplates during heat sealing or any other application of heat that may induce warpage. Additionally, the devices and methods provided herein can be useful in stabilizing and/or securing microplates, including tubes and/or wells, during heat sealing or during any other stage of manipulating, processing, and/or preparing reagents that may require minimal movement of the microplate (e.g., an automated volume verification step using a sensor).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A schematically illustrates an isometric view of the base plate. FIG. 2B schematically illustrates a top view of the base plate. FIG. 2C schematically illustrates a side view of the base plate.

FIG. 3A schematically illustrates an isometric view of the post. FIG. 3B schematically illustrates a side view of the post. FIG. 3C schematically illustrates a top view of the post.

FIG. 4A schematically illustrates a top view of the aligner. FIG. 4B schematically illustrates a side view of the aligner. FIG. 4C schematically illustrates a bottom view of the aligner.

FIG. 5A schematically illustrates an isometric view of the frame. FIG. 5B schematically illustrates a top view of the frame. FIG. 5C schematically illustrates a side view of the frame.

FIG. 6A schematically illustrates a microplate holder and a base plate comprising tabs. FIG. 6B schematically illustrates the microplate holder and the base plate assembled together.

FIGS. 7A-7D schematically illustrate various views of an example of a base plate of the microplate holder. FIG. 7A schematically illustrates an isometric view of the base plate. FIG. 7B schematically illustrates a top view of the base plate. FIG. 7C schematically illustrates a first side view of the base plate. FIG. 7D schematically illustrates a second side view of the base plate.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

The terminology used herein is for the purpose of describing particular cases only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

The term "about" or "approximately," as used herein, refers to an amount that is near the stated amount by about 10%, 5%, or 1%, including increments therein. For example, "about" or "approximately" may mean a range including the particular value and ranging from 10% below that particular value and spanning to 10% above that particular value.

The term "microplate," as used herein, refers to a microwell plate, a multiwell plate, a flat plate with at least one well, a microtiter plate, a flat plate with individual test tubes, a flat plate with interconnected test tubes, a flat plate with test tube strips, a flat plate with at least one removable well, a skirted microplate, a semi-skirted microplate, a non-skirted microplate, a segment of a microplate, or a breakaway microplate.

Figure 1:
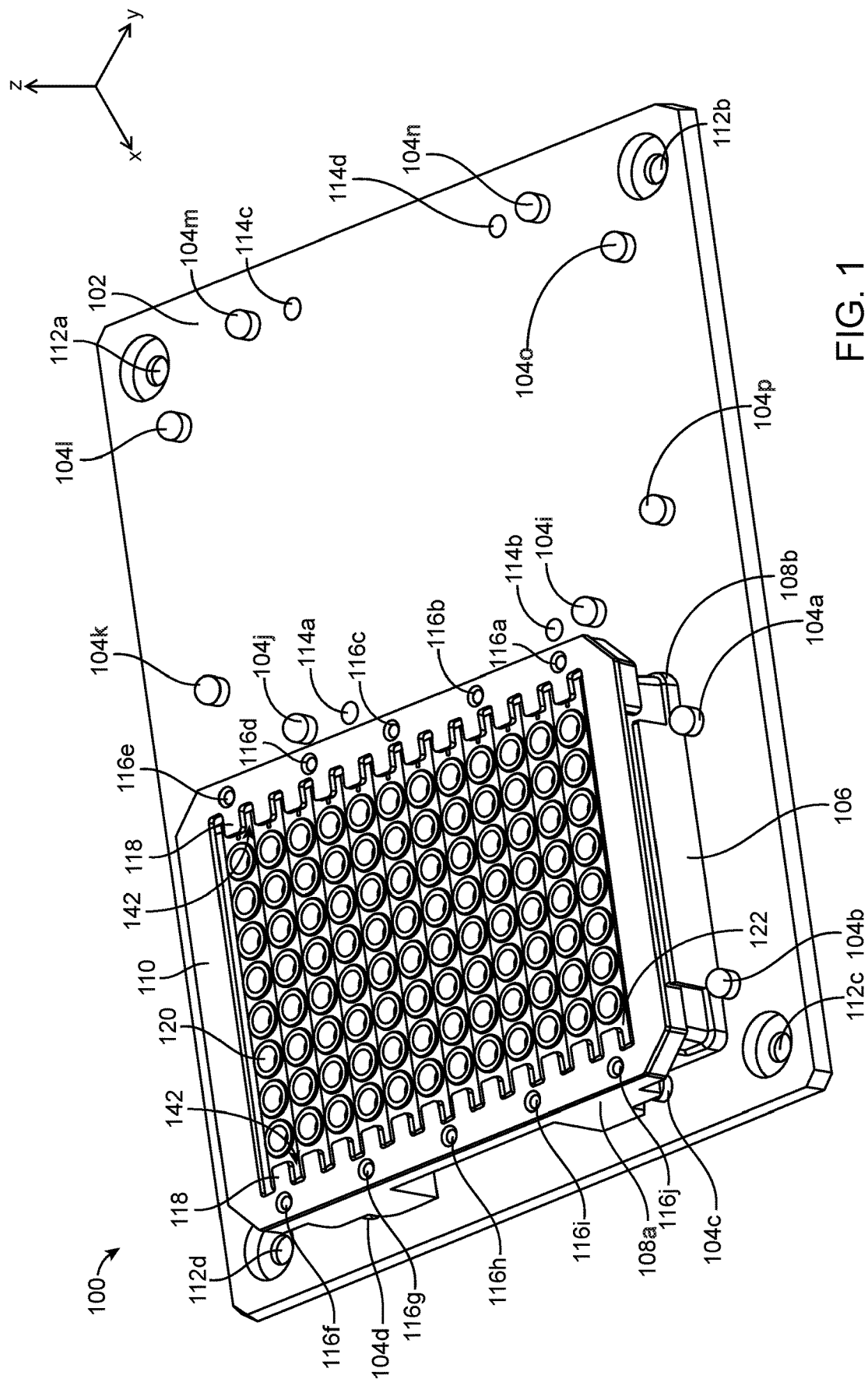
FIG. 1 schematically illustrates an example of a microplate holder.

The term "proximal," as used herein refers to the top side or the side of the material or element that faces towards the user when the microplate holder is assembled (e.g., as shown in FIG. 1).

The term "distal," as used herein refers to the bottom side or the side of the material or element that faces away from the user when the microplate holder is assembled (e.g., as shown in FIG. 1).

Described herein are devices and methods that may be useful for immobilizing micro-well or micro-titer plates (including those having receptacles, such as tubes) in their wells. In some cases, such methods and devices are used to keep a micro-well or micro-titer plate and/or tube strips in a flat position. In some cases, such methods and devices may be used to prevent warpage of microplates and/or tubes during an application of heat (e.g., during heat sealing). In some cases, devices and methods described herein are used to visualize wells in a micro-well or micro-titer plate (including tubes in such wells) to determine whether or not fluid (e.g., pipetted fluid) has been added to the wells. For example, the devices and methods described herein may work synergistically with an automated liquid handling device that may perform a volume verification operation. Devices and methods described herein may also be suitable for use with heat sealing of cover sheets (e.g., aluminum cover sheets) that can cover one or more wells and/or tubes of a micro-well or micro-titer plate. In some cases, a plate sealer may be used to heat seal the cover sheets. Devices and methods described herein may also be suitable for use with laser cutting of plastic tubes (e.g., tube strips) that can be contained within the wells of a micro-titer plate.

Provided herein is a flat plate with an opening to keep well contents (e.g., tubes) flat and allow access (including visual access) to the wells (and, thus, tubes) for checking liquid level, including for use in systems including laser cutting systems or mechanisms. The plate may be mounted to two spacer/aligners which hold magnets that may produce force that is sufficient to keep it in place and a spacer to position it. The magnets in the two spacer/aligners may be attracted to magnets on a base plate, to ferric metal posts on a base plate or even a ferric metal base plate.

The present disclosure provides devices and methods for securing microplates. In an aspect, a microplate holder for securing a microplate comprises: a base plate; an aligner configured to accept the microplate, wherein the aligner comprises a proximal surface, a distal surface, and an attraction unit between the proximal surface and the distal surface, which attraction unit is attractable towards the base plate to position the aligner adjacent to the base plate; and a frame configured to rest adjacent to the aligner and a proximal surface of the microplate, wherein the frame comprises a plurality of projections that extend along a direction parallel to the proximal surface of the aligner when the frame is positioned adjacent to the aligner.

In another aspect, the present disclosure provides a method of securing a microplate, comprising: attaching a microplate holder to the microplate, the microplate holder comprising: a base plate; an aligner configured to accept said microplate, wherein the aligner comprises a proximal surface, a distal surface, and an attraction unit between the proximal surface and the distal surface, which attraction unit is attractable towards the base plate to position the aligner adjacent to the base plate; and a frame configured to rest adjacent to the aligner and a proximal surface of the microplate, wherein the frame comprises a plurality of projections that extend along a direction parallel to the proximal surface of the aligner when the frame is positioned adjacent to the aligner.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Microplate Holder Devices

In an aspect, as illustrated in FIG. 1, the present disclosure provides a microplate holder 100 for securing a microplate. The microplate holder 100 may prevent or restrict movement of the microplate. The movement may be a lateral movement, a longitudinal movement, or a proximal movement away from a base plate. The microplate may be a microwell plate. The microplate may be a multiwell plate. The microplate may be a flat plate with at least one well. The microplate may be a microtiter plate. The microplate may be a flat plate comprising individual test tubes. The microplate may be a flat plate comprising interconnected test tubes. The microplate may be a flat plate comprising test tube strips. The microplate may be a flat plate comprising at least one removable well. The microplate may be a skirted microplate. The microplate may be a semi-skirted microplate. The microplate may be a non-skirted microplate. The microplate may be a segment of a microplate. The microplate may be a breakaway microplate. The microplate 106 may have a top surface 122, as shown in FIG. 1.

The microplate 106 may have a plurality of wells 120. The microplate may have a number of wells ranging from at least about 1 well to about 2000 well or more. The microplate may have about 1 well. The microplate may have about 4 wells. The microplate may have about 6 wells. The microplate may have about 8 wells. The microplate may have about 12 wells. The microplate may have about 24 wells. The microplate may have about 48 wells. The microplate may have about 96 wells. The microplate may have about 384 wells. The microplate may have about 1536 wells.

The microplate may have about 1 well to about 1,536 wells. The microplate may have at least about 1 well. The microplate may have at most about 1,536 wells. The microplate may have about 1 well to about 4 wells, about 1 well to about 6 wells, about 1 well to about 12 wells, about 1 well to about 48 wells, about 1 well to about 96 wells, about 1 well to about 384 wells, about 1 well to about 1,536 wells, about 4 wells to about 6 wells, about 4 wells to about 12 wells, about 4 wells to about 48 wells, about 4 wells to about 96 wells, about 4 wells to about 384 wells, about 4 wells to about 1,536 wells, about 6 wells to about 12 wells, about 6 wells to about 48 wells, about 6 wells to about 96 wells, about 6 wells to about 384 wells, about 6 wells to about 1,536 wells, about 12 wells to about 48 wells, about 12 wells to about 96 wells, about 12 wells to about 384 wells, about 12 wells to about 1,536 wells, about 48 wells to about 96 wells, about 48 wells to about 384 wells, about 48 wells to about 1,536 wells, about 96 wells to about 384 wells, about 96 wells to about 1,536 wells, or about 384 wells to about 1,536 wells. The microplate may have about 1 well, about 4 wells, about 6 wells, about 12 wells, about 48 wells, about 96 wells, about 384 wells, or about 1,536 wells.

The microplate may have a well volume of at least about 1 µl to about 500 µl or more. The microplate may have a well volume of at least about 1 µl. The microplate may have a well volume of at most about 500 µl. The microplate may have a well volume of about 1 µl to about 10 µl, about 1 µl to about 20 µl, about 1 µl to about 50 µl, about 1 µl to about 75 µl, about 1 µl to about 100 µl, about 1 µl to about 125 µl, about 1 µl to about 150 µl, about 1 µl to about 175 µl, about 1 µl to about 200 µl, about 1 µl to about 300 µl, about 1 µl to about 500 µl , about 10 µl to about 20 µl, about 10 µl to about 50 µl, about 10 µl to about 75 µl, about 10 µl to about 100 µl, about 10 µl to about 125 µl, about 10 µl to about 150 µl, about 10 µl to about 175 µl, about 10 µl to about 200 µl, about 10 µl to about 300 µl, about 10 µl to about 500 µl, about 20 µl to about 50 µl, about 20 µl to about 75 µl, about 20 µl to about 100 µl, about 20 µl to about 125 µl, about 20 µl to about 150 µl, about 20 µl to about 175 µl, about 20 µl to about 200 µl, about 20 µl to about 300 µl, about 20 µl to about 500 µl, about 50 µl to about 75 µl, about 50 µl to about 100 µl, about 50 µl to about 125 µl, about 50 µl to about 150 µl, about 50 µl to about 175 µl, about 50 µl to about 200 µl, about 50 µl to about 300 µl, about 50 µl to about 500 µl, about 75 µl to about 100 µl, about 75 µl to about 125 µl, about 75 µl to about 150 µl, about 75 µl to about 175 µl, about 75 µl to about 200 µl, about 75 µl to about 300 µl, about 75 µl to about 500 µl, about 100 µl to about 125 µl, about 100 µl to about 150 µl, about 100 µl to about 175 µl, about 100 µl to about 200 µl, about 100 µl to about 300 µl, about 100 µl to about 500 µl, about 125 µl to about 150 µl, about 125 µl to about 175 µl, about 125 µl to about 200 µl, about 125 µl to about 300 µl, about 125 µl to about 500 µl, about 150 µl to about 175 µl, about 150 µl to about 200 µl, about 150 µl to about 300 µl, about 150 µl to about 500 µl, about 175 µl to about 200 µl, about 175 µl to about 300 µl, about 175 µl to about 500 µl, about 200 µl to about 300 µl, about 200 µl to about 500 µl, or about 300 µl to about 500 µl. The microplate may have a well volume of about 1 µl, about 10 µl, about 20 µl, about 50 µl, about 75 µl, about 100 µl, about 125 µl, about 150 µl, about 175 µl, about 200 µl, about 300 µl, or about 500 µl.

Figure 2A:
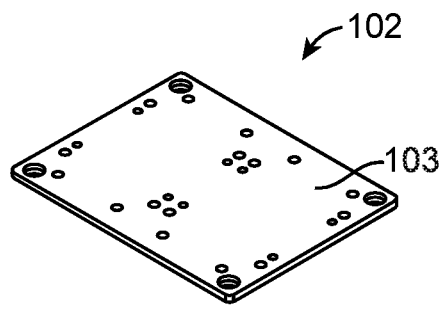
FIGS. 2A-2C schematically illustrate various views of an example of a base plate of a microplate holder.

FIG. 1 shows an example of a microplate holder 100 for securing a microplate 106. The microplate holder 100 may comprise a base plate 102, an aligner 108, a frame 110, or a combination thereof. The base plate 102 may be rectangular in shape, as shown also in FIGS. 1 and 2A-2B. The base plate may be circular, square, or any other shape that is able to support the bottom surface of the microplate or a portion of the bottom surface of the microplate. FIG. 2A illustrates an isometric view of the base plate 102 and shows the proximal surface of the base plate 103. The proximal surface of the base plate 103 is defined herein as the side of the base plate that faces the user when the microplate holder is assembled, as shown in FIGS. 2A and 2C. The distal surface of the base plate 105 is defined herein as the side of the base plate that faces away from the user when the microplate holder is assembled, as shown in FIG. 2C.

Figure 2B:
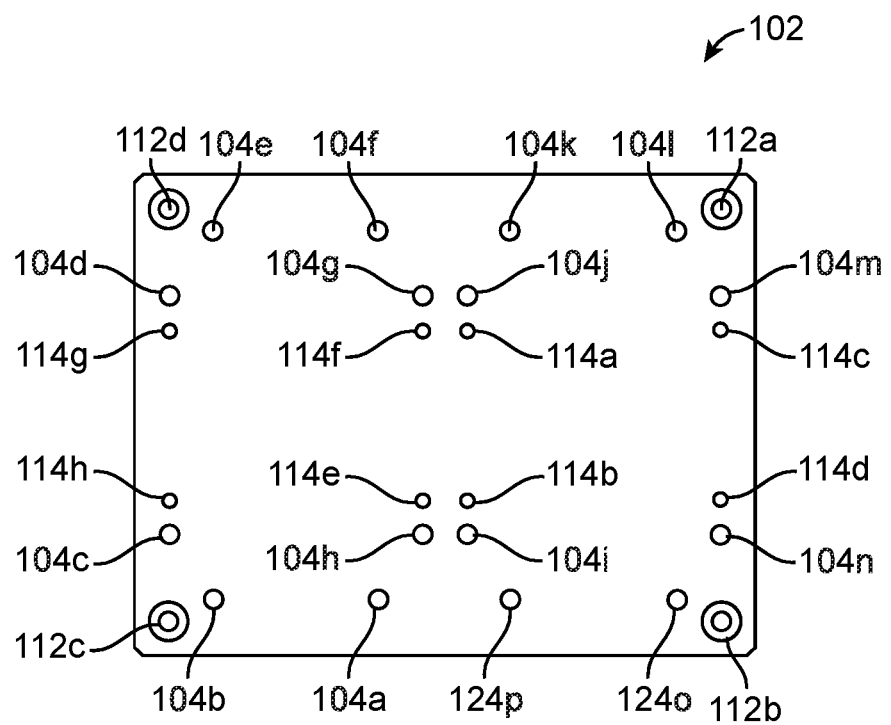
Figure 2C:
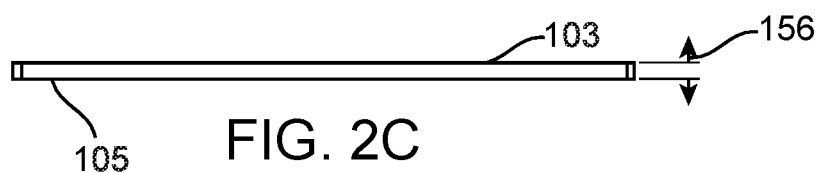

FIG. 2B illustrates a top view of the base plate 102. The base plate may accommodate one or two microplates. As shown in FIG. 2B, the base plate 102 may comprise a first base plate hole 112a, a second base plate hole 112b, a third base plate hole 112c, and a fourth base plate hole 112d. The base plate holes may be configured to receive a screw that may be used to secure the base plate to any surface. Alternatively, the base plate may comprise an adhesive or a double-sided adhesive for adhering to any surface. The base plate may comprise one or more grooves that may interlock with a connector on a surface. The base plate may be secured to any surface by a magnetic force. The base plate may be a ferromagnetic material that is attractable towards a surface with an opposite polarity.

The base plate may comprise an additional attraction unit. For example, FIG. 1 shows the base plate comprising a first attraction unit 114a, a second attraction unit 114b, a third attraction unit 114c, and a fourth attraction unit 114d. FIG. 2B shows the base plate may comprise a first attraction unit 114a, a second attraction unit 114b, a third attraction unit 114c, a fourth attraction unit 114d, a fifth attraction unit 114e, a sixth attraction unit 114f, a seventh attraction unit 114g, and an eighth attraction unit 114h. The attraction units on the base plate may abut the distal surface of the aligner. The attraction unit may be placed on the proximal surface of the base plate 103. The attraction unit may be permanently attached to the base plate. The attraction unit may be reversibly attached to the base plate. For example, the attraction unit may be reversibly secured to the base plate by a snap fixture, a screw, a magnetic force, a pin, or any combination thereof.

The base plate may comprise about 1 attraction unit to about 20 attraction units. The base plate may comprise at least about 1 attraction unit. The base plate may comprise at most about 20 attraction units. The base plate may comprise about 1 attraction unit to about 2 attraction units, about 1 attraction unit to about 3 attraction units, about 1 attraction unit to about 4 attraction units, about 1 attraction unit to about 5 attraction units, about 1 attraction unit to about 6 attraction units, about 1 attraction unit to about 7 attraction units, about 1 attraction unit to about 8 attraction units, about 1 attraction unit to about 9 attraction units, about 1 attraction unit to about 10 attraction units, about 1 attraction unit to about 15 attraction units, about 1 attraction unit to about 20 attraction units, about 2 attraction units to about 3 attraction units, about 2 attraction units to about 4 attraction units, about 2 attraction units to about 5 attraction units, about 2 attraction units to about 6 attraction units, about 2 attraction units to about 7 attraction units, about 2 attraction units to about 8 attraction units, about 2 attraction units to about 9 attraction units, about 2 attraction units to about 10 attraction units, about 2 attraction units to about 15 attraction units, about 2 attraction units to about 20 attraction units, about 3 attraction units to about 4 attraction units, about 3 attraction units to about 5 attraction units, about 3 attraction units to about 6 attraction units, about 3 attraction units to about 7 attraction units, about 3 attraction units to about 8 attraction units, about 3 attraction units to about 9 attraction units, about 3 attraction units to about 10 attraction units, about 3 attraction units to about 15 attraction units, about 3 attraction units to about 20 attraction units, about 4 attraction units to about 5 attraction units, about 4 attraction units to about 6 attraction units, about 4 attraction units to about 7 attraction units, about 4 attraction units to about 8 attraction units, about 4 attraction units to about 9 attraction units, about 4 attraction units to about 10 attraction units, about 4 attraction units to about 15 attraction units, about 4 attraction units to about 20 attraction units, about 5 attraction units to about 6 attraction units, about 5 attraction units to about 7 attraction units, about 5 attraction units to about 8 attraction units, about 5 attraction units to about 9 attraction units, about 5 attraction units to about 10 attraction units, about 5 attraction units to about 15 attraction units, about 5 attraction units to about 20 attraction units, about 6 attraction units to about 7 attraction units, about 6 attraction units to about 8 attraction units, about 6 attraction units to about 9 attraction units, about 6 attraction units to about 10 attraction units, about 6 attraction units to about 15 attraction units, about 6 attraction units to about 20 attraction units, about 7 attraction units to about 8 attraction units, about 7 attraction units to about 9 attraction units, about 7 attraction units to about 10 attraction units, about 7 attraction units to about 15 attraction units, about 7 attraction units to about 20 attraction units, about 8 attraction units to about 9 attraction units, about 8 attraction units to about 10 attraction units, about 8 attraction units to about 15 attraction units, about 8 attraction units to about 20 attraction units, about 9 attraction units to about 10 attraction units, about 9 attraction units to about 15 attraction units, about 9 attraction units to about 20 attraction units, about 10 attraction units to about 15 attraction units, about 10 attraction units to about 20 attraction units, or about 15 attraction units to about 20 attraction units. The base plate may comprise about 1 attraction unit, about 2 attraction units, about 3 attraction units, about 4 attraction units, about 5 attraction units, about 6 attraction units, about 7 attraction units, about 8 attraction units, about 9 attraction units, about 10 attraction units, about 15 attraction units, or about 20 attraction units.

The attraction unit on the base plate may be a magnet. The magnet may be a permanent magnet. The magnet may be an electromagnet. The magnet may be a ferromagnetic material. The base plate or a portion thereof may be a ferromagnetic material. The ferromagnetic material may be copper, iron, ferric oxide, iron (II, III) oxide, manganese, nickel, yttrium iron garnet, chromium dioxide, gadolinium, terbium, dysprosium, trevorite, europium oxide, or a combination thereof. The ferromagnetic material may be cobalt, ferritic stainless steel, martensitic stainless steel, or a combination thereof.

The base plate may be a metal, a plastic, an elastomer material, or a combination thereof. The base plate may be a non-ferromagnetic metal. Non-limiting examples of the non-ferromagnetic metal include aluminum, aluminum alloys, copper, lead, nickel, tin, titanium, zinc, brass, and annealed austenitic stainless steel. The base plate may be a ferromagnetic material. The ferromagnetic material may be copper, iron, ferric oxide, iron (II, III) oxide, manganese, nickel, yttrium iron garnet, chromium dioxide, gadolinium, terbium, dysprosium, trevorite, europium oxide, or a combination thereof. The ferromagnetic material may be cobalt, ferritic stainless steel, martensitic stainless steel, or a combination thereof. The base plate may be a plastic or an elastomeric material. Non-limiting examples of a plastic or an elastomer material include polyethylene, polypropylene, polystyrene, polyester, polylactic acid (PLA), polycarbonate, polyvinyl chloride, polyethersulfone, polyacrylate, acrylic, polymethylmethacrylate (PMMA), polysulfone, polyetheretherketone (PEEK), thermoplastic elastomers, thermoplastic urethanes, poly-p-xylylene, and parylene.

As shown in FIG. 2B, the base plate 102 may comprise a first post 104a, a second post 104b, a third post 104c, a fourth post 104d, a fifth post 104e, a sixth post 104f, a seventh post 104g, an eighth post 104h, a ninth post 104i, a tenth post 104j, an eleventh post 104k, a twelfth post 104l, a thirteenth post 104m, a fourteenth post 104n, a fifteenth post 104o, and a sixteenth post 104p. FIG. 1 does not show the fifth post 104e, the sixth post 104f, the seventh post 104g, and the eighth post 104h. The posts may extend upwardly from the base plate. The posts may extend from the base plate along a z-axis, as shown in FIG. 1. The post 104 may project upward from the surface of the base plate. To secure the microplate with the microplate holder, the microplate 106 may be placed on top of the base plate 102 and within the area enclosed by the plurality of posts. For example, FIG. 1 shows the microplate 106 abutting the first post 104a, the second post 104b, the third post 104c and the fourth post 104d. The microplate 106 may also abut two additional posts on its right side, not shown in FIG. 1. Additionally, a second microplate can be placed on the base plate 102, within the space created by the ninth post 104i, the tenth post 104j, the eleventh post 104k, the twelfth post 104l, the thirteenth post 104m, the fourteenth post 104n, the fifteenth post 104o, and the sixteenth post 104p. The second microplate can abut the ninth post 104i, the tenth post 104j, the eleventh post 104k, the twelfth post 104l, the thirteenth post 104m, the fourteenth post 104n, the fifteenth post 104o, and the sixteenth post 104p, once aligned.

FIG. 2C schematically illustrates a side view of the base plate 102. The base plate may comprise a thickness 156. The thickness 156 of the base plate 102 may be at least about 0.1 centimeters (cm) to about 1.5 cm or more. The thickness 156 of the base plate 102 may be at least about 0.1 cm. The thickness 156 of the base plate 102 may be at most about 1.5 cm. The thickness 156 of the base plate 102 may be about 0.1 cm to about 0.2 cm, about 0.1 cm to about 0.3 cm, about 0.1 cm to about 0.4 cm, about 0.1 cm to about 0.5 cm, about 0.1 cm to about 0.6 cm, about 0.1 cm to about 0.7 cm, about 0.1 cm to about 0.8 cm, about 0.1 cm to about 0.9 cm, about 0.1 cm to about 1 cm, about 0.1 cm to about 1.5 cm, about 0.2 cm to about 0.3 cm, about 0.2 cm to about 0.4 cm, about 0.2 cm to about 0.5 cm, about 0.2 cm to about 0.6 cm, about 0.2 cm to about 0.7 cm, about 0.2 cm to about 0.8 cm, about 0.2 cm to about 0.9 cm, about 0.2 cm to about 1 cm, about 0.2 cm to about 1.5 cm, about 0.3 cm to about 0.4 cm, about 0.3 cm to about 0.5 cm, about 0.3 cm to about 0.6 cm, about 0.3 cm to about 0.7 cm, about 0.3 cm to about 0.8 cm, about 0.3 cm to about 0.9 cm, about 0.3 cm to about 1 cm, about 0.3 cm to about 1.5 cm, about 0.4 cm to about 0.5 cm, about 0.4 cm to about 0.6 cm, about 0.4 cm to about 0.7 cm, about 0.4 cm to about 0.8 cm, about 0.4 cm to about 0.9 cm, about 0.4 cm to about 1 cm, about 0.4 cm to about 1.5 cm, about 0.5 cm to about 0.6 cm, about 0.5 cm to about 0.7 cm, about 0.5 cm to about 0.8 cm, about 0.5 cm to about 0.9 cm, about 0.5 cm to about 1 cm, about 0.5 cm to about 1.5 cm, about 0.6 cm to about 0.7 cm, about 0.6 cm to about 0.8 cm, about 0.6 cm to about 0.9 cm, about 0.6 cm to about 1 cm, about 0.6 cm to about 1.5 cm, about 0.7 cm to about 0.8 cm, about 0.7 cm to about 0.9 cm, about 0.7 cm to about 1 cm, about 0.7 cm to about 1.5 cm, about 0.8 cm to about 0.9 cm, about 0.8 cm to about 1 cm, about 0.8 cm to about 1.5 cm, about 0.9 cm to about 1 cm, about 0.9 cm to about 1.5 cm, or about 1 cm to about 1.5 cm. The thickness 156 of the base plate 102 may be about 0.1 cm, about 0.2 cm, about 0.3 cm, about 0.4 cm, about 0.5 cm, about 0.6 cm, about 0.7 cm, about 0.8 cm, about 0.9 cm, about 1 cm, or about 1.5 cm.

Figure 3A:
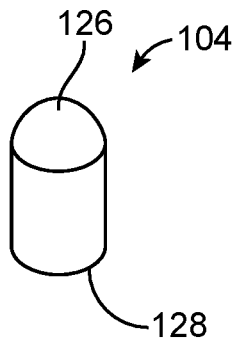
FIGS. 3A-3C schematically illustrate various views of an example of a post of a microplate holder.
Figure 3B:
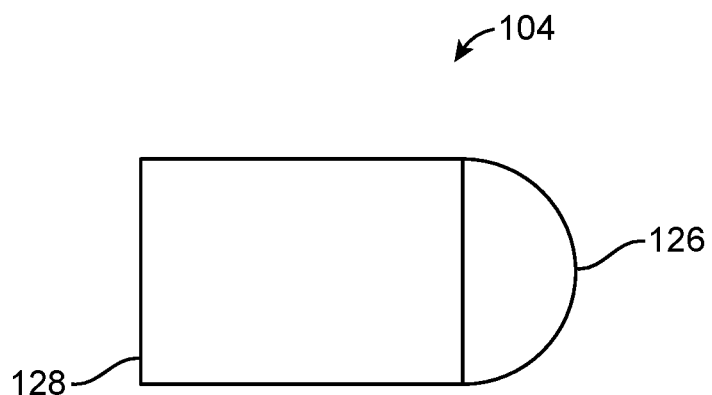
Figure 3C:
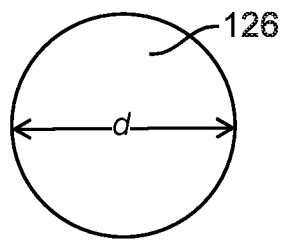

FIG. 3A schematically illustrates an isometric view of one post 104. The post 104 may comprise a proximal end 126 and a distal end 128. The proximal end 126 may be shaped like a hemispherical dome. The proximal end 126 may be shaped like a cone, a cylinder, a cube, cuboid, or any combination thereof. The proximal end 126 may comprise a planar surface. The proximal end 126 may further comprise a connector configured to reversibly attach to a surface or a cavity. The proximal end 126 may further comprise an attraction unit. The proximal end 126 may further comprise a magnet. The proximal end 126 may be a ferromagnetic material. The distal end 128 may comprise a flat or planar surface. The distal end 128 may be in connection with the base plate or a portion thereof. FIG. 3C schematically illustrates a top view of the post 104 which shows the proximal end 126.

The height of the post 104 may be defined by the distance between the proximal end 126 and the distal end 128. The height of the post 104 may be about 1.25 centimeters (cm). The height of the post 104 may be at least about 0.5 cm to about 3 cm or more. The height of the post 104 may be at least about 0.5 cm. The height of the post 104 may be at most about 3 cm. The height of the post 104 may be about 0.5 cm to about 0.6 cm, about 0.5 cm to about 0.7 cm, about 0.5 cm to about 0.8 cm, about 0.5 cm to about 0.9 cm, about 0.5 cm to about 1 cm, about 0.5 cm to about 1.25 cm, about 0.5 cm to about 1.5 cm, about 0.5 cm to about 1.75 cm, about 0.5 cm to about 2 cm, about 0.5 cm to about 3 cm, about 0.6 cm to about 0.7 cm, about 0.6 cm to about 0.8 cm, about 0.6 cm to about 0.9 cm, about 0.6 cm to about 1 cm, about 0.6 cm to about 1.25 cm, about 0.6 cm to about 1.5 cm, about 0.6 cm to about 1.75 cm, about 0.6 cm to about 2 cm, about 0.6 cm to about 3 cm, about 0.7 cm to about 0.8 cm, about 0.7 cm to about 0.9 cm, about 0.7 cm to about 1 cm, about 0.7 cm to about 1.25 cm, about 0.7 cm to about 1.5 cm, about 0.7 cm to about 1.75 cm, about 0.7 cm to about 2 cm, about 0.7 cm to about 3 cm, about 0.8 cm to about 0.9 cm, about 0.8 cm to about 1 cm, about 0.8 cm to about 1.25 cm, about 0.8 cm to about 1.5 cm, about 0.8 cm to about 1.75 cm, about 0.8 cm to about 2 cm, about 0.8 cm to about 3 cm, about 0.9 cm to about 1 cm, about 0.9 cm to about 1.25 cm, about 0.9 cm to about 1.5 cm, about 0.9 cm to about 1.75 cm, about 0.9 cm to about 2 cm, about 0.9 cm to about 3 cm, about 1 cm to about 1.25 cm, about 1 cm to about 1.5 cm, about 1 cm to about 1.75 cm, about 1 cm to about 2 cm, about 1 cm to about 3 cm, about 1.25 cm to about 1.5 cm, about 1.25 cm to about 1.75 cm, about 1.25 cm to about 2 cm, about 1.25 cm to about 3 cm, about 1.5 cm to about 1.75 cm, about 1.5 cm to about 2 cm, about 1.5 cm to about 3 cm, about 1.75 cm to about 2 cm, about 1.75 cm to about 3 cm, or about 2 cm to about 3 cm. The height of the post 104 may be about 0.5 cm, about 0.6 cm, about 0.7 cm, about 0.8 cm, about 0.9 cm, about 1 cm, about 1.25 cm, about 1.5 cm, about 1.75 cm, about 2 cm, or about 3 cm.

The diameter of the post 104 may be defined as the diameter of the proximal end 126 labeled as d, as shown in FIG. 3C. The diameter of the post 104 may be about 0.6 cm. The diameter of the post 104 may be at least about 0.5 cm to about 1 cm or more. The diameter of the post 104 may be at least about 0.5 cm. The diameter of the post 104 may be at most about 1 cm. The diameter of the post 104 may be about 0.5 cm to about 0.6 cm, about 0.5 cm to about 0.7 cm, about 0.5 cm to about 0.8 cm, about 0.5 cm to about 0.9 cm, about 0.5 cm to about 1 cm, about 0.6 cm to about 0.7 cm, about 0.6 cm to about 0.8 cm, about 0.6 cm to about 0.9 cm, about 0.6 cm to about 1 cm, about 0.7 cm to about 0.8 cm, about 0.7 cm to about 0.9 cm, about 0.7 cm to about 1 cm, about 0.8 cm to about 0.9 cm, about 0.8 cm to about 1 cm, or about 0.9 cm to about 1 cm. The diameter of the post 104 may be about 0.5 cm, about 0.6 cm, about 0.7 cm, about 0.8 cm, about 0.9 cm, or about 1 cm.

The post 104 may be a stainless steel material. The post may be a ferromagnetic material. The ferromagnetic material may be copper, iron, ferric oxide, iron (II, III) oxide, manganese, nickel, yttrium iron garnet, chromium dioxide, gadolinium, terbium, dysprosium, trevorite, europium oxide, or a combination thereof. The ferromagnetic material may be cobalt, ferritic stainless steel, martensitic stainless steel, or a combination thereof. The post may be a non-ferromagnetic metal. Non-limiting examples of the non-ferromagnetic metal include aluminum, aluminum alloys, copper, lead, nickel, tin, titanium, zinc, brass, and annealed austenitic stainless steel. The post may be stainless steel AISI (American Iron and Steel Institute) 304. The post may be stainless steel AISI (American Iron and Steel Institute) 302. The post may be stainless steel AISI (American Iron and Steel Institute) 316 or 316L. The post may be electropolished stainless steel.

The base plate may comprise at least about 1 post to about 48 posts or more. The base plate may comprise at least about 1 post. The base plate may comprise at most about 48 posts. The base plate may comprise about 1 post to about 2 posts, about 1 post to about 3 posts, about 1 post to about 4 posts, about 1 post to about 8 posts, about 1 post to about 16 posts, about 1 post to about 24 posts, about 1 post to about 32 posts, about 1 post to about 40 posts, about 1 post to about 48 posts, about 2 posts to about 3 posts, about 2 posts to about 4 posts, about 2 posts to about 8 posts, about 2 posts to about 16 posts, about 2 posts to about 24 posts, about 2 posts to about 32 posts, about 2 posts to about 40 posts, about 2 posts to about 48 posts, about 3 posts to about 4 posts, about 3 posts to about 8 posts, about 3 posts to about 16 posts, about 3 posts to about 24 posts, about 3 posts to about 32 posts, about 3 posts to about 40 posts, about 3 posts to about 48 posts, about 4 posts to about 8 posts, about 4 posts to about 16 posts, about 4 posts to about 24 posts, about 4 posts to about 32 posts, about 4 posts to about 40 posts, about 4 posts to about 48 posts, about 8 posts to about 16 posts, about 8 posts to about 24 posts, about 8 posts to about 32 posts, about 8 posts to about 40 posts, about 8 posts to about 48 posts, about 16 posts to about 24 posts, about 16 posts to about 32 posts, about 16 posts to about 40 posts, about 16 posts to about 48 posts, about 24 posts to about 32 posts, about 24 posts to about 40 posts, about 24 posts to about 48 posts, about 32 posts to about 40 posts, about 32 posts to about 48 posts, or about 40 posts to about 48 posts. The base plate may comprise about 1 post, about 2 posts, about 3 posts, about 4 posts, about 8 posts, about 16 posts, about 24 posts, about 32 posts, about 40 posts, or about 48 posts.

The base plate 102 may comprise one or more posts that are attractable towards an attraction unit on the aligner. The attraction unit may be a magnet. In some cases, the aligner may be a ferromagnetic material. The base plate 102 may comprise one or more posts that are attractable towards a ferromagnetic aligner. The one or more posts may comprise an additional attraction unit. The additional attraction unit may be a magnet. The magnet may be a permanent magnet. The magnet may be an electromagnet. The magnet may be a ferromagnetic material. The ferromagnetic material may be copper, iron, ferric oxide, iron (II, III) oxide, manganese, nickel, yttrium iron garnet, chromium dioxide, gadolinium, terbium, dysprosium, trevorite, europium oxide, or a combination thereof. The ferromagnetic material may be cobalt, ferritic stainless steel, martensitic stainless steel, or a combination thereof. The base plate 102 may comprise one or more posts comprising an additional attraction unit that is attractable towards an attraction unit on the aligner. The base plate 102 may comprise one or more posts comprising an additional attraction unit that is attractable towards a ferromagnetic aligner.

The attraction unit may comprise an electrode that supplies an electric field from the electrode to the aligner, or vice versa. The additional attraction unit may comprise an electrode that supplies an electric field from the electrode to the aligner, or vice versa. The electrode may supply an electric field from the electrode to the base plate, or vice versa. The electrode may supply an electric field from the electrode to one or more posts, or vice versa. The electrode may supply an electric field from the electrode to the frame, or vice versa. The electrode may be negatively charged. The electrode may be positively charged. The electrode and the aligner may comprise opposite electric charges. The electrode and the aligner may comprise opposite polarities. The electric field may be an electromagnetic field. The electric field supplied from the electrode to the aligner may cause the aligner to be attracted to a material with an opposite polarity. In some cases, the material with a polarity opposite to that of the aligner may be the frame. In some cases, the material with a polarity opposite to that of the aligner may be the base plate. In some cases, the material with a polarity opposite to that of the aligner may be one or more posts. The electric field supplied from the electrode to the base plate may cause the base plate to be attracted to a material with an opposite polarity. In some cases, the material with a polarity opposite to that of the base plate may be the frame. In some cases, the material with a polarity opposite to that of the base plate may be the aligner. In some cases, the material with a polarity opposite to that of the base plate may be one or more posts. The electric field supplied from the electrode to the frame may cause the frame to be attracted to a material with an opposite polarity. In some cases, the material with a polarity opposite to that of the frame may be the aligner. In some cases, the material with a polarity opposite to that of the frame may be the base plate. In some cases, the material with a polarity opposite to that of the frame may be one or more posts. The electric field supplied from the electrode to one or more posts may cause one or more posts to be attracted to a material with an opposite polarity. In some cases, the material with a polarity opposite to that of one or more posts may be the frame. In some cases, the material with a polarity opposite to that of one or more posts may be the base plate. In some cases, the material with a polarity opposite to that of one or more posts may be the aligner.

The one or more posts may be configured to abut at least one edge of the microplate. The one or more posts may restrict a lateral or longitudinal movement of the microplate. The plurality of posts on the base plate may align the microplate. The plurality of posts on the base plate may prevent a horizontal or a vertical displacement of the microplate. The plurality of posts on the base plate may secure the microplate. The base plate 102 may comprise one or more posts that are permanently coupled to the aligner. In some cases, the base plate and the aligner may be permanently coupled by the one or more posts. The base plate 102 may comprise one or more posts that are reversibly coupled to the aligner. For example, the aligner may comprise a cavity, recess, hole, pocket, or groove configured to receive the one or more posts or a connector. The one or more posts may mate with a recess, hole, pocket, or groove in a distal surface of the aligner. In some cases, the one or more posts may serve as a boss that connects to a cavity, recess, hole, pocket, or groove in the aligner. The one or more posts may comprise a reversibly engaging locking mechanism comprising a connector that connects the one or more posts to the aligner. The connector may be capable of connecting and/or locking the one or more posts to the aligner. In some cases, the connector may be an internal locking ring that rests on a post and mates with one or more notches located on the distal surface of the aligner.

Figure 4A:
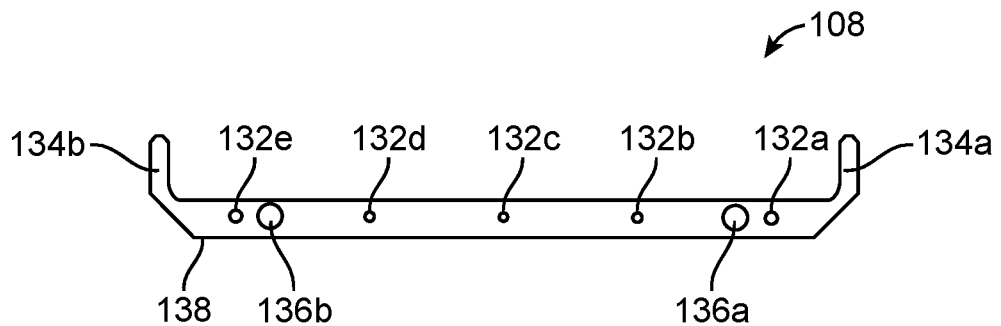
FIGS. 4A-4C schematically illustrate various views of an example of an aligner of a microplate holder.

FIG. 4A schematically illustrates a top view of the aligner 108 (i.e., the proximal view of the aligner). The aligner may be configured to accept the microplate. The aligner may comprise a proximal surface, a distal surface, and an attraction unit between the proximal surface and the distal surface. The attraction unit may be attractable towards the base plate to position the aligner adjacent to the base plate. The aligner 108 may comprise a first aligner hole 132*a*, a second aligner hole 132*b*, a third aligner hole 132*c*, a fourth aligner hole 132*d*, and a fifth aligner hole 132*e*. The aligner hole may not extend from the proximal surface of the aligner 138 to the distal surface of the aligner 140. The aligner hole may extend from the proximal surface of the aligner 138 to the distal surface of the aligner 140. The aligner hole may be a threaded aligner hole. The aligner hole may comprise one or more spiraling threads. The one or more spiraling threads may be located on the interior wall of the aligner hole. The spiraling thread can be any suitable type of thread that can receive a screw. The spiraling thread may have a pitch of at least about 0.4 millimeters (mm) to about 1.5 mm. The spiraling thread may have a pitch of at least about 0.4 mm. The spiraling thread may have a pitch of at most about 1.5 mm. The spiraling thread may have a pitch of about 0.4 mm to about 0.45 mm, about 0.4 mm to about 0.5 mm, about 0.4 mm to about 0.7 mm, about 0.4 mm to about 0.8 mm, about 0.4 mm to about 1 mm, about 0.4 mm to about 1.25 mm, about 0.4 mm to about 1.5 mm, about 0.45 mm to about 0.5 mm, about 0.45 mm to about 0.7 mm, about 0.45 mm to about 0.8 mm, about 0.45 mm to about 1 mm, about 0.45 mm to about 1.25 mm, about 0.45 mm to about 1.5 mm, about 0.5 mm to about 0.7 mm, about 0.5 mm to about 0.8 mm, about 0.5 mm to about 1 mm, about 0.5 mm to about 1.25 mm, about 0.5 mm to about 1.5 mm, about 0.7 mm to about 0.8 mm, about 0.7 mm to about 1 mm, about 0.7 mm to about 1.25 mm, about 0.7 mm to about 1.5 mm, about 0.8 mm to about 1 mm, about 0.8 mm to about 1.25 mm, about 0.8 mm to about 1.5 mm, about 1 mm to about 1.25 mm, about 1 mm to about 1.5 mm, or about 1.25 mm to about 1.5 mm. The spiraling thread may have a pitch of about 0.4 mm, about 0.45 mm, about 0.5 mm, about 0.7 mm, about 0.8 mm, about 1 mm, about 1.25 mm, or about 1.5 mm.

Figure 4B:
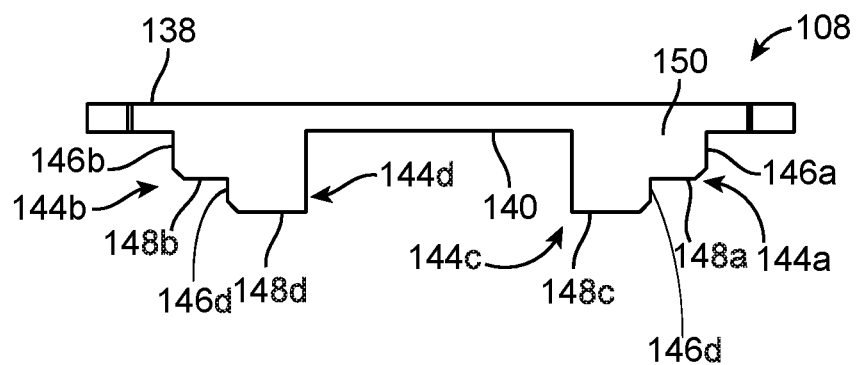
Figure 4C:
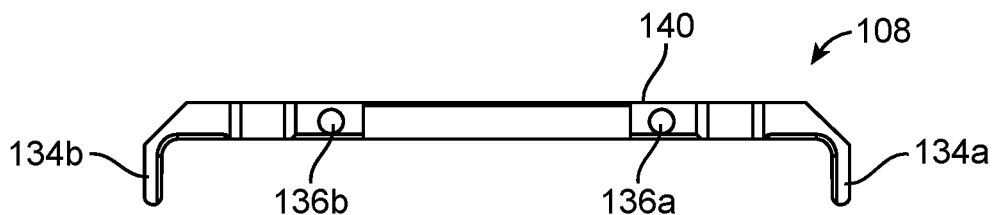

The aligner 108 may comprise a first arm 134*a* and a second arm 134*b*, as shown in FIG. 4A. The first arm 134*a* and a second arm 134*b* may be protruding members of the aligner that align with a first corner and a second corner of the microplate when the aligner 108 is placed on a lateral, top surface of the microplate. The aligner may further comprise a first arm extending from a first end of the lateral wall and a second arm extending from a second end of the lateral wall. The first arm may surround a first corner of the microplate and the second arm may surround a second corner of the microplate. The aligner 108 may comprise a first attraction unit 136*a* and a second attraction unit 136*b*, as shown in FIGS. 4A and 4C. The first attraction unit 136*a* may be a first magnet. The second attraction unit 136*b* may be a second magnet. FIG. 4B schematically illustrates a side view of the aligner 108. The aligner may comprise a lateral wall 150. The lateral wall 150 may face away from the microplate when assembled (e.g., as shown in FIG. 1). The aligner may comprise a first step 144*a*, a second step 144*b*, a third step 144*c*, and a fourth step 144*d*. The first step 144*a* may comprise a first vertical wall 146*a* and a first horizontal surface 148*a*. The first vertical wall 146*a* extends downward and meets the first horizontal surface 148*a*; thus, forming the first step 144*a*. Similarly, the second step 144*b* may comprise a second vertical wall 146*b* and a second horizontal surface 148*b*. The second vertical wall 146*b* extends downward and meets the second horizontal surface 148*b*; thus, forming the second step 144*b*. Likewise, the third step 144*c* may comprise a third vertical wall 146*c* and a third horizontal surface 148*c*. The third vertical wall 146*c* extends downward and meets the third horizontal surface 148*c*; thus, forming the third step 144*c*. Correspondingly, the fourth step 144*d* may comprise a fourth vertical wall 146*d* and a fourth horizontal surface 148*d*. The fourth vertical wall 146*d* extends downward and meets the fourth horizontal surface 148*d*; thus, forming the fourth step 144*d*. The step structures in the aligner may help position the aligner on the base plate, posts, and/or microplate. For example, when the microplate holder is assembled, the third horizontal surface 148*c* and the fourth horizontal surface 148*d* may rest adjacent to the proximal or top surface of the base plate. Furthermore, when the microplate holder is assembled, the first horizontal surface 148*a* and the second horizontal surface 148*b* may rest adjacent to the proximal end 126 of one or more posts. Additional attraction units may be placed on the first horizontal surface 148*a*, the second horizontal surface 148*b*, the third horizontal surface 148*c*, and/or the fourth horizontal surface 148*d* to further secure the aligner to the base plate and/or one or more posts.

A first aligner and a second aligner may be placed onto a first lateral surface and a second lateral surface of the microplate. In some cases, the first and second aligners may be connected to form one single piece. The distal surface of the aligner or a portion thereof may rest adjacent to the proximal end 126 of a post. FIG. 1 shows a first aligner 108*a* resting adjacent to the left lateral surface of the microplate and a second aligner 108*b* resting adjacent to the right lateral surface of the microplate. In addition, FIG. 1 shows the first aligner 108*a* resting adjacent to the third post 108*c* and the fourth post 108*d*. The aligner may comprise one or more additional holes in its distal surface. For example, the aligner may comprise one or more additional holes in the first horizontal surface 148*a*, the second horizontal surface 148*b*, the third horizontal surface 148*c*, and/or the fourth horizontal surface 148*d*. The one or more additional holes may comprise inner screw threads. The aligner holes may comprise inner screw threads. As used herein, a screw is used generically to refer to screws, bolts, studs, pins, rivets, anchors, or any other attachment device that is used for the secure attachment of two materials. For example, the screw may be a standard screw that may have a head shaped to receive a Phillips screwdriver or a flat head screwdriver. Alternatively, the screw may have another standard or non-standard shaped screw head. The screw may be placed through a hole in the base plate and screwed into a threaded aligner hole in the aligner. When tightened, a screw may hold the base plate tightly against the distal surface of the aligner. When tightened, a screw may hold the base plate tightly against the third horizontal surface 148*c* of the aligner. When tightened, a screw may hold the base plate tightly against the fourth horizontal surface 148*d* of the aligner.

Figure 5A:
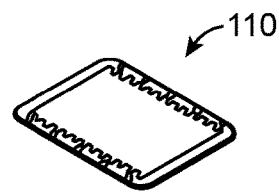
FIGS. 5A-5C schematically illustrate various view of n example of a frame of the microplate holder.
Figure 5B:
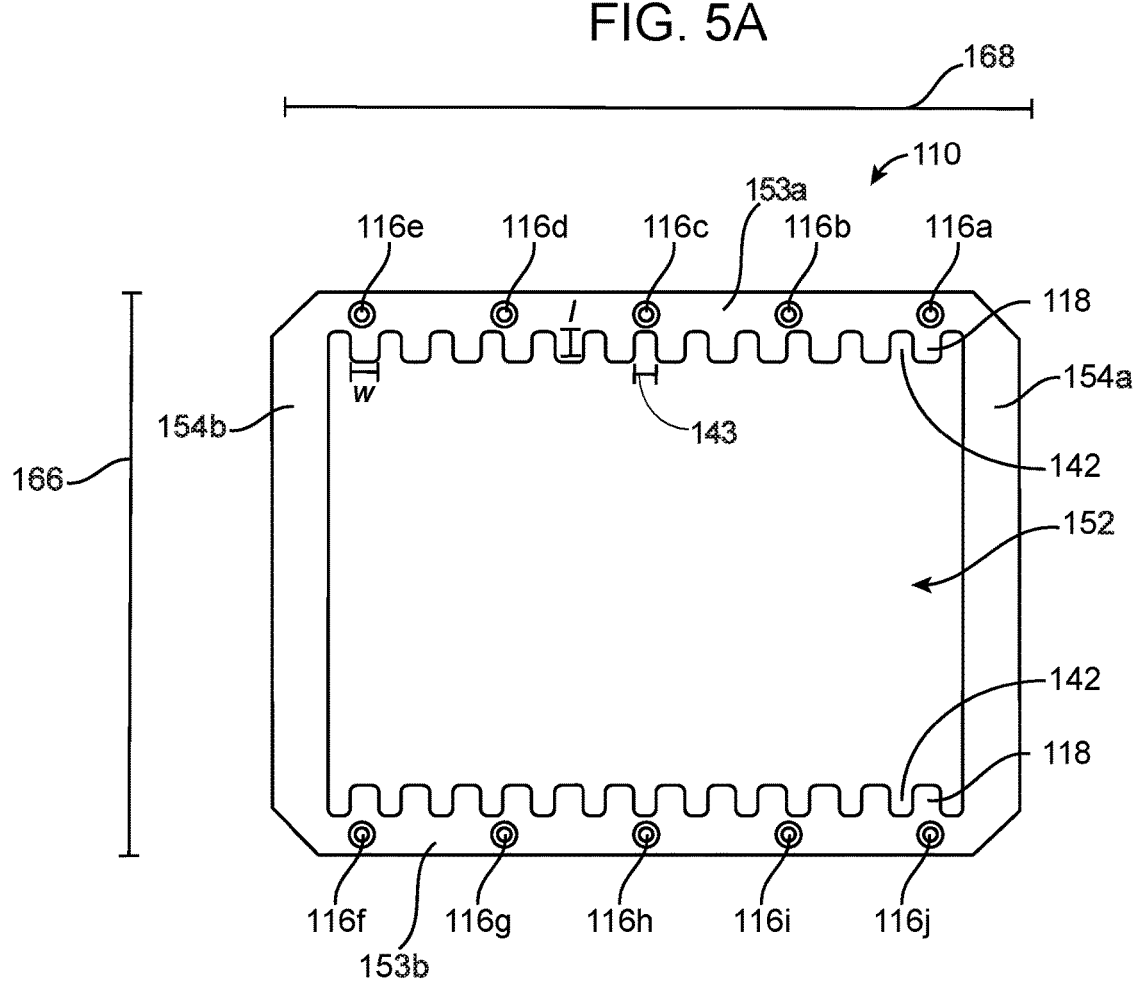

The microplate holder may comprise a frame configured to rest adjacent to the aligner and a proximal surface of the microplate. FIG. 5A schematically illustrates an isometric view of the frame 110. FIG. 5B schematically illustrates a top view of the frame 110. The frame 110 may have a rectangular shape that conforms to the edges of the microplate. The frame 110 may comprise a first narrow side 154*a*, a second narrow side 154*b*, a first broad side 153*a*, and a second broad side 153*b* that together enclose an opening 152, as shown in FIG. 5B. The first narrow side 154*a* and the second narrow side 154*b* may have a length (shown as 166 in FIG. 5B) of about 10 cm. The first narrow side 154*a* and the second narrow side 154*b* may have a length of at least about 5 cm to about 20 cm or more. The first narrow side 154*a* and the second narrow side 154*b* may have a length of at least about 5 cm. The first narrow side 154a and the second narrow side 154b may have a length of at most about 20 cm. The first narrow side 154a and the second narrow side 154b may have a length of about 5 cm to about 6 cm, about 5 cm to about 7 cm, about 5 cm to about 8 cm, about 5 cm to about 9 cm, about 5 cm to about 10 cm, about 5 cm to about 15 cm, about 5 cm to about 20 cm, about 6 cm to about 7 cm, about 6 cm to about 8 cm, about 6 cm to about 9 cm, about 6 cm to about 10 cm, about 6 cm to about 15 cm, about 6 cm to about 20 cm, about 7 cm to about 8 cm, about 7 cm to about 9 cm, about 7 cm to about 10 cm, about 7 cm to about 15 cm, about 7 cm to about 20 cm, about 8 cm to about 9 cm, about 8 cm to about 10 cm, about 8 cm to about 15 cm, about 8 cm to about 20 cm, about 9 cm to about 10 cm, about 9 cm to about 15 cm, about 9 cm to about 20 cm, about 10 cm to about 15 cm, about 10 cm to about 20 cm, or about 15 cm to about 20 cm. The first narrow side 154a and the second narrow side 154b may have a length of about 5 cm, about 6 cm, about 7 cm, about 8 cm, about 9 cm, about 10 cm, about 15 cm, or about 20 cm.

The first broad side 153a and the second broad side 153b may have a length (shown as 168 in FIG. 5B) of about 13 cm. The first broad side 153a and the second broad side 153b may have a length of at least about 5 cm to about 20 cm or more. The first broad side 153a and the second broad side 153b may have a length of at least about 5 cm. The first broad side 153a and the second broad side 153b may have a length of at most about 20 cm. The first broad side 153a and the second broad side 153b may have a length of about 5 cm to about 6 cm, about 5 cm to about 7 cm, about 5 cm to about 8 cm, about 5 cm to about 9 cm, about 5 cm to about 10 cm, about 5 cm to about 13 cm, about 5 cm to about 15 cm, about 5 cm to about 20 cm, about 6 cm to about 7 cm, about 6 cm to about 8 cm, about 6 cm to about 9 cm, about 6 cm to about 10 cm, about 6 cm to about 13 cm, about 6 cm to about 15 cm, about 6 cm to about 20 cm, about 7 cm to about 8 cm, about 7 cm to about 9 cm, about 7 cm to about 10 cm, about 7 cm to about 13 cm, about 7 cm to about 15 cm, about 7 cm to about 20 cm, about 8 cm to about 9 cm, about 8 cm to about 10 cm, about 8 cm to about 13 cm, about 8 cm to about 15 cm, about 8 cm to about 20 cm, about 9 cm to about 10 cm, about 9 cm to about 13 cm, about 9 cm to about 15 cm, about 9 cm to about 20 cm, about 10 cm to about 13 cm, about 10 cm to about 15 cm, about 10 cm to about 20 cm, about 13 cm to about 15 cm, about 13 cm to about 20 cm, or about 15 cm to about 20 cm. The first broad side 153a and the second broad side 153b may have a length of about 5 cm, about 6 cm, about 7 cm, about 8 cm, about 9 cm, about 10 cm, about 13 cm, about 15 cm, or about 20 cm.

The frame 110 may be a rigid, open structure that can rest adjacent to the proximal or top surface of the microplate and at least one aligner. The frame 110 may be sized to fit over the microplate 106 so that the edges of the frame 110 are contacted with at least one of the outer edges of the proximal surface or top surface of the plate. The frame may comprise at least one projection 118. The frame 110 may comprise a plurality of projections 118, as shown in FIG. 5B. The frame may comprise a plurality of projections that extend along a direction parallel to the proximal surface of the aligner when the frame is positioned adjacent to the aligner. The projection 118 may have a rectangular shape, a square shape, a circular shape, or a triangular shape. The projection 118 may have any shape that has a surface area that is sufficiently large to cover a narrow side of a row of wells in the microplate or a portion thereof. Each projection 118 may extend from a first broad side 153a and/or from a second broad side 153b of the frame 110 towards the center of a microplate. Each projection 118 may cover the surface of the narrow side of a row of wells in a microplate. Each projection 118 may cover the surface of the narrow side of a multiwell strip in a microplate. Each projection 118 may cover the surface of the narrow side of a multiwell strip in a microplate. Each projection 118 may align with a row of wells 120.

The microplate 106 may further comprise one or more strips of tubes (i.e., tube strips). For example, the microwell plate comprises tube strips instead of rows of wells. Alternatively, one or more tube strips may be placed in a microplate 106 (e.g., a tube strip may be fitted into a row of wells). Each projection 118 may align with a strip of tubes (i.e., a tube strip) in a microplate 106. A tube strip may comprise of a row of tubes held together by a frame. A tube strip may comprise at least two tubes. A tube strip may comprise at least three tubes. A tube strip may comprise at least four tubes. A tube strip may comprise at least five tubes. A tube strip may comprise at least six tubes. A tube strip may comprise at least seven tubes. A tube strip may comprise eight tubes. A tube strip may be a one-piece tube strip or a two-component tube strip. A one-piece tube strip may comprise a flexible frame that holds the tubes together. A two-component tube strip may comprise a molded frame that is more rigid compared to the flexible frame of the one-piece tube strip. A tube strip may be used for a polymerase chain reaction (PCR) assay or any other assay requiring the manipulation of reagents in volumes ranging from at least about 1 microliter (µl) to about 1000 µl.

The tube strip may comprise tubes with a volume capacity of at least about 1 µl to about 1,000 µl or more. The tube strip may comprise tubes with a volume capacity of at least about 1 µl. The tube strip may comprise tubes with a volume capacity of at most about 1,000 µl. The tube strip may comprise tubes with a volume capacity of about 1 µl to about 50 µl, about 1 µl to about 100 µl, about 1 µl to about 200 µl, about 1 µl to about 300 µl, about 1 µl to about 400 µl, about 1 µl to about 500 µl, about 1 µl to about 600 µl, about 1 µl to about 700 µl, about 1 µl to about 800 µl, about 1 µl to about 900 µl, about 1 µl to about 1,000 µl, about 50 µl to about 100 µl, about 50 µl to about 200 µl, about 50 µl to about 300 µl, about 50 µl to about 400 µl, about 50 µl to about 500 µl, about 50 µl to about 600 µl, about 50 µl to about 700 µl, about 50 µl to about 800 µl, about 50 µl to about 900 µl, about 50 µl to about 1,000 µl, about 100 µl to about 200 µl, about 100 µl to about 300 µl, about 100 µl to about 400 µl, about 100 µl to about 500 µl, about 100 µl to about 600 µl, about 100 µl to about 700 µl, about 100 µl to about 800 µl, about 100 µl to about 900 µl, about 100 µl to about 1,000 µl, about 200 µl to about 300 µl, about 200 µl to about 400 µl, about 200 µl to about 500 µl, about 200 µl to about 600 µl, about 200 µl to about 700 µl, about 200 µl to about 800 µl, about 200 µl to about 900 µl, about 200 µl to about 1,000 µl, about 300 µl to about 400 µl, about 300 µl to about 500 µl, about 300 µl to about 600 µl, about 300 µl to about 700 µl, about 300 µl to about 800 µl, about 300 µl to about 900 µl, about 300 µl to about 1,000 µl, about 400 µl to about 500 µl, about 400 µl to about 600 µl, about 400 µl to about 700 µl, about 400 µl to about 800 µl, about 400 µl to about 900 µl, about 400 µl to about 1,000 µl, about 500 µl to about 600 µl, about 500 µl to about 700 µl, about 500 µl to about 800 µl, about 500 µl to about 900 µl, about 500 µl to about 1,000 µl, about 600 µl to about 700 µl, about 600 µl to about 800 µl, about 600 µl to about 900 µl, about 600 µl to about 1,000 µl, about 700 µl to about 800 µl, about 700 µl to about 900 µl, about 700 µl to about 1,000 µl, about 800

μl to about 900 μl, about 800 μl to about 1,000 μl, or about 900 μl to about 1,000 μl. The tube strip may comprise tubes with a volume capacity of about 1 μl, about 50 μl, about 100 μl, about 200 μl, about 300 μl, about 400 μl, about 500 μl, about 600 μl, about 700 μl, about 800 μl, about 900 μl, or about 1,000 μl.

Each projection 118 may align with a tube strip in a microplate. The tube strip may have a first end and a second end which correspond to the narrow sides of the tube strip. Each projection 118 may secure a tube strip placed in the microplate 106 by making contact with the planar top surface of a first end and/or a second end of the tube strip. The frame 110 may secure the tube strip by contacting a narrow side of the tube strip with a projection 118. The frame may prevent movement of the tube strip along an x-, y-, or z-axis. The frame may prevent a dimensional distortion or warpage of the tube strip (e.g., when exposing the tube strip to heat).

The projection 118 may have a width (shown as w in FIG. 5B) of about 5 millimeters (mm). The projection 118 may have a width of at least about 5 mm to about 15 mm or more. The projection 118 may have a width of at least about 5 mm. The projection 118 may have a width of at most about 15 mm. The projection 118 may have a width of about 5 mm to about 6 mm, about 5 mm to about 7 mm, about 5 mm to about 8 mm, about 5 mm to about 9 mm, about 5 mm to about 10 mm, about 5 mm to about 15 mm, about 6 mm to about 7 mm, about 6 mm to about 8 mm, about 6 mm to about 9 mm, about 6 mm to about 10 mm, about 6 mm to about 15 mm, about 7 mm to about 8 mm, about 7 mm to about 9 mm, about 7 mm to about 10 mm, about 7 mm to about 15 mm, about 8 mm to about 9 mm, about 8 mm to about 10 mm, about 8 mm to about 15 mm, about 9 mm to about 10 mm, about 9 mm to about 15 mm, or about 10 mm to about 15 mm. The projection 118 may have a width of about 5 mm, about 6 mm, about 7 mm, about 8 mm, about 9 mm, about 10 mm, or about 15 mm.

The projection 118 may have a length (shown as l in FIG. 5B) of about 5 millimeters (mm). The projection 118 may have a length of at least about 5 mm to about 15 mm or more. The projection 118 may have a length of at least about 5 mm. The projection 118 may have a length of at most about 15 mm. The projection 118 may have a length of about 5 mm to about 6 mm, about 5 mm to about 7 mm, about 5 mm to about 8 mm, about 5 mm to about 9 mm, about 5 mm to about 10 mm, about 5 mm to about 15 mm, about 6 mm to about 7 mm, about 6 mm to about 8 mm, about 6 mm to about 9 mm, about 6 mm to about 10 mm, about 6 mm to about 15 mm, about 7 mm to about 8 mm, about 7 mm to about 9 mm, about 7 mm to about 10 mm, about 7 mm to about 15 mm, about 8 mm to about 9 mm, about 8 mm to about 10 mm, about 8 mm to about 15 mm, about 9 mm to about 10 mm, about 9 mm to about 15 mm, or about 10 mm to about 15 mm. The projection 118 may have a length of about 5 mm, about 6 mm, about 7 mm, about 8 mm, about 9 mm, about 10 mm, or about 15 mm.

The projections may form a recess 142, as shown in FIGS. 1 and 5B. The recesses may provide a space along each edge of a narrow side of a tube strip or a row of wells in a microplate. The recesses may provide access to an instrument, such as a laser cutter, along each edge of a narrow side of a tube strip or a row of wells in a microplate. The recess 142 may have a width of 4 mm; recess width 143 is illustrated in FIG. 5B. The recess 142 may have a width of at least about 3 mm to about 15 mm or more. The recess 142 may have a width of at least about 3 mm. The recess 142 may have a width of at most about 15 mm. The recess 142 may have a width of about 3 mm to about 4 mm, about 3 mm to about 5 mm, about 3 mm to about 6 mm, about 3 mm to about 7 mm, about 3 mm to about 8 mm, about 3 mm to about 9 mm, about 3 mm to about 10 mm, about 3 mm to about 15 mm, about 4 mm to about 5 mm, about 4 mm to about 6 mm, about 4 mm to about 7 mm, about 4 mm to about 8 mm, about 4 mm to about 9 mm, about 4 mm to about 10 mm, about 4 mm to about 15 mm, about 5 mm to about 6 mm, about 5 mm to about 7 mm, about 5 mm to about 8 mm, about 5 mm to about 9 mm, about 5 mm to about 10 mm, about 5 mm to about 15 mm, about 6 mm to about 7 mm, about 6 mm to about 8 mm, about 6 mm to about 9 mm, about 6 mm to about 10 mm, about 6 mm to about 15 mm, about 7 mm to about 8 mm, about 7 mm to about 9 mm, about 7 mm to about 10 mm, about 7 mm to about 15 mm, about 8 mm to about 9 mm, about 8 mm to about 10 mm, about 8 mm to about 15 mm, about 9 mm to about 10 mm, about 9 mm to about 15 mm, or about 10 mm to about 15 mm. The recess 142 may have a width of about 3 mm, about 4 mm, about 5 mm, about 6 mm, about 7 mm, about 8 mm, about 9 mm, about 10 mm, or about 15 mm.

The frame may be configured to be reversibly attached to the aligner. The frame 110 may be placed on the proximal surface of the aligner 138. The frame may comprise a first frame hole 116*a*, a second frame hole 116*b*, a third frame hole 116*c*, a fourth frame hole 116*d*, a fifth frame hole 116*e*, a sixth frame hole 116*f*, a seventh frame hole 116*g*, an eighth frame hole 116*h*, a ninth frame hole 116*i*, and a tenth frame hole 116*j*. The frame holes may extend from the proximal or top surface of the frame to the distal or bottom surface of the frame (i.e., through the thickness 158 of the frame). The frame holes may be located on the edge of the frame and laterally adjacent to the projections. The frame holes may be aligned linearly along the first broad side 153*a* and/or the second broad side 153*b* of the frame 110. The frame may comprise at least one frame hole configured to align with at least one aligner hole. The at least one frame hole and the at least one aligner hole may be configured to accept a screw or a securing pin. The screw or the securing pin may anchor the frame and the aligner together. The frame may comprise one or more snapping tabs extending from a side of the frame. The one or more snapping tabs may make a mechanical contact with one or more aligner snapping tab apertures. The frame 110 may be secured to the first aligner 108*a* and the second aligner 108*b* by insertion of a fastening device, e.g., a screw, through a frame hole and into an aligner hole. An aligner hole may comprise inner screw threads. The screw may be placed through a frame hole in the frame 110 and screwed into a threaded aligner hole in the aligner. When tightened, the screw may hold the frame 110 tightly against the proximal surface of the aligner 138 (not shown in FIG. 1).

Figure 5C:
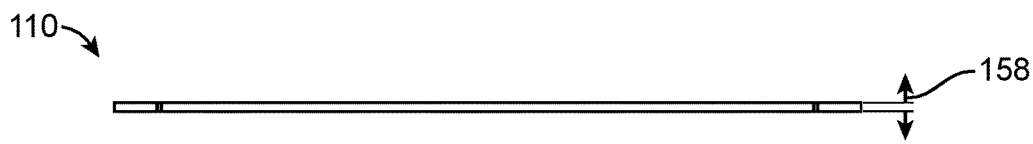

The frame 110 may comprise blunt corners. The frame 110 may comprise a thickness 158, as shown in FIG. 5C. The frame 110 may comprise a thickness 158 of about 1.5 mm. The frame 110 may comprise a thickness 158 of at least about 1 mm to about 10 mm or more. The frame 110 may comprise a thickness 158 of at least about 1 mm. The frame 110 may comprise a thickness 158 of at most about 10 mm. The frame 110 may comprise a thickness 158 of about 1 mm to about 1.5 mm, about 1 mm to about 2 mm, about 1 mm to about 3 mm, about 1 mm to about 4 mm, about 1 mm to about 5 mm, about 1 mm to about 10 mm, about 1.5 mm to about 2 mm, about 1.5 mm to about 3 mm, about 1.5 mm to about 4 mm, about 1.5 mm to about 5 mm, about 1.5 mm to about 10 mm, about 2 mm to about 3 mm, about 2 mm to about 4 mm, about 2 mm to about 5 mm, about 2 mm to about 10 mm, about 3 mm to about 4 mm, about 3 mm to about 5 mm, about 3 mm to about 10 mm, about 4 mm to about 5 mm, about 4 mm to about 10 mm, or about 5 mm to about 10 mm. The frame 110 may comprise a thickness 158 of about 1 mm, about 1.5 mm, about 2 mm, about 3 mm, about 4 mm, about 5 mm, or about 10 mm.

The frame 110 may comprise an additional attraction unit. The additional attraction unit may be a magnet. The magnet may be a permanent magnet. The magnet may be an electromagnet. The magnet may be a ferromagnetic material. The ferromagnetic material may be copper, iron, ferric oxide, iron (II, III) oxide, manganese, nickel, yttrium iron garnet, chromium dioxide, gadolinium, terbium, dysprosium, trevorite, europium oxide, or a combination thereof. The additional attraction unit may comprise an electrode that supplies an electric field from the electrode to the base plate, or vice versa. The additional attraction unit may be attractable towards the aligner to position the frame adjacent to the aligner and the proximal surface of the microplate.

The frame 110 may be a stainless steel material. The frame 110 may be stainless steel AISI (American Iron and Steel Institute) 304. The frame 110 may be stainless steel AISI (American Iron and Steel Institute) 302. The frame 110 may be stainless steel AISI (American Iron and Steel Institute) 316 or 316L. The frame 110 may be electropolished stainless steel. The frame 110 may be a ferromagnetic material. The ferromagnetic material may be copper, iron, ferric oxide, iron (II, III) oxide, manganese, nickel, yttrium iron garnet, chromium dioxide, gadolinium, terbium, dysprosium, trevorite, europium oxide, or a combination thereof. The ferromagnetic material may be cobalt, ferritic stainless steel, martensitic stainless steel, or a combination thereof. The frame 110 may be a non-ferromagnetic metal. Non-limiting examples of the non-ferromagnetic metal include aluminum, aluminum alloys, copper, lead, nickel, tin, titanium, zinc, brass, and annealed austenitic stainless steel.

Figure 6A:
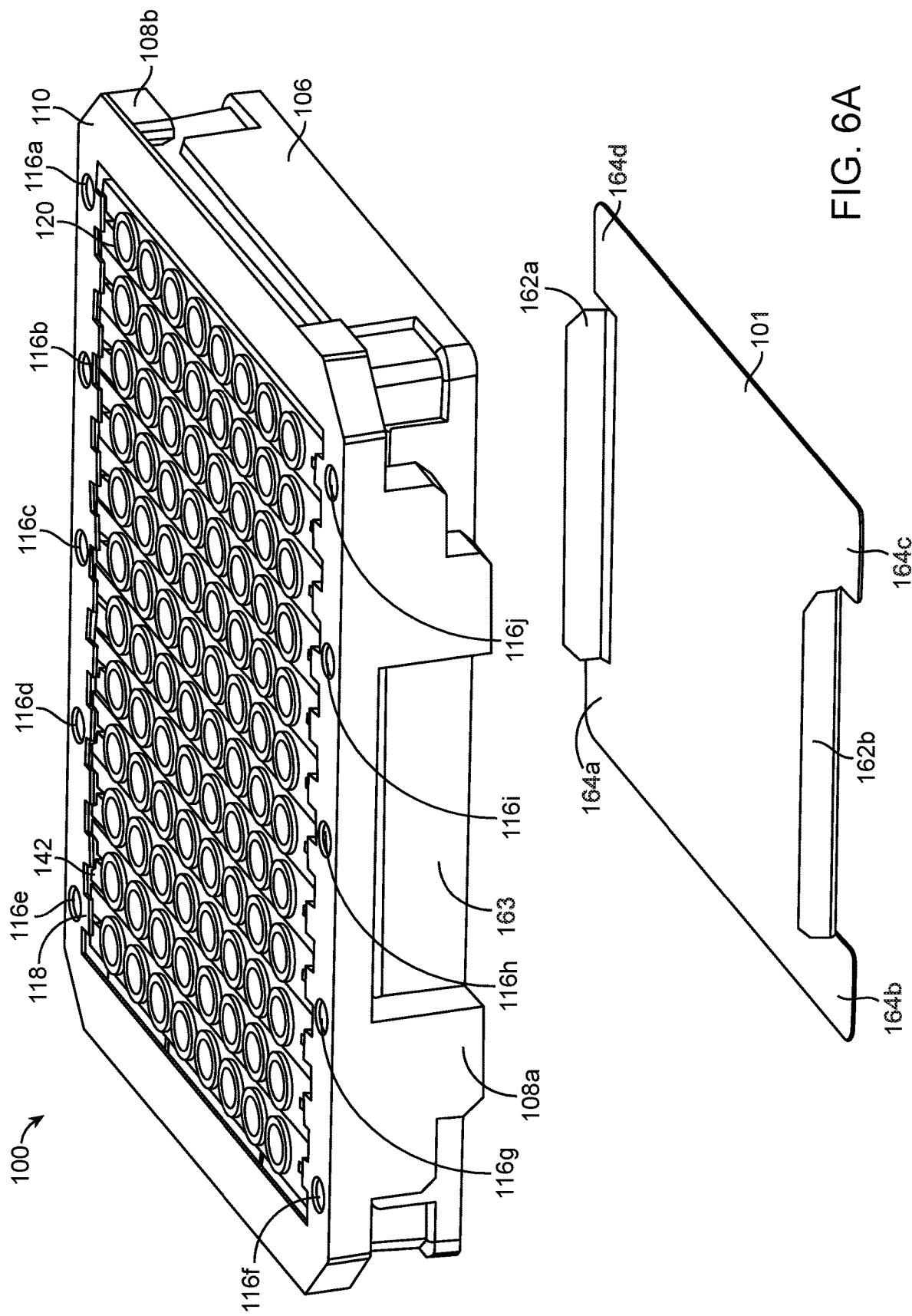
FIGS. 6A-6B schematically illustrate an example of a microplate holder.
Figure 6B:
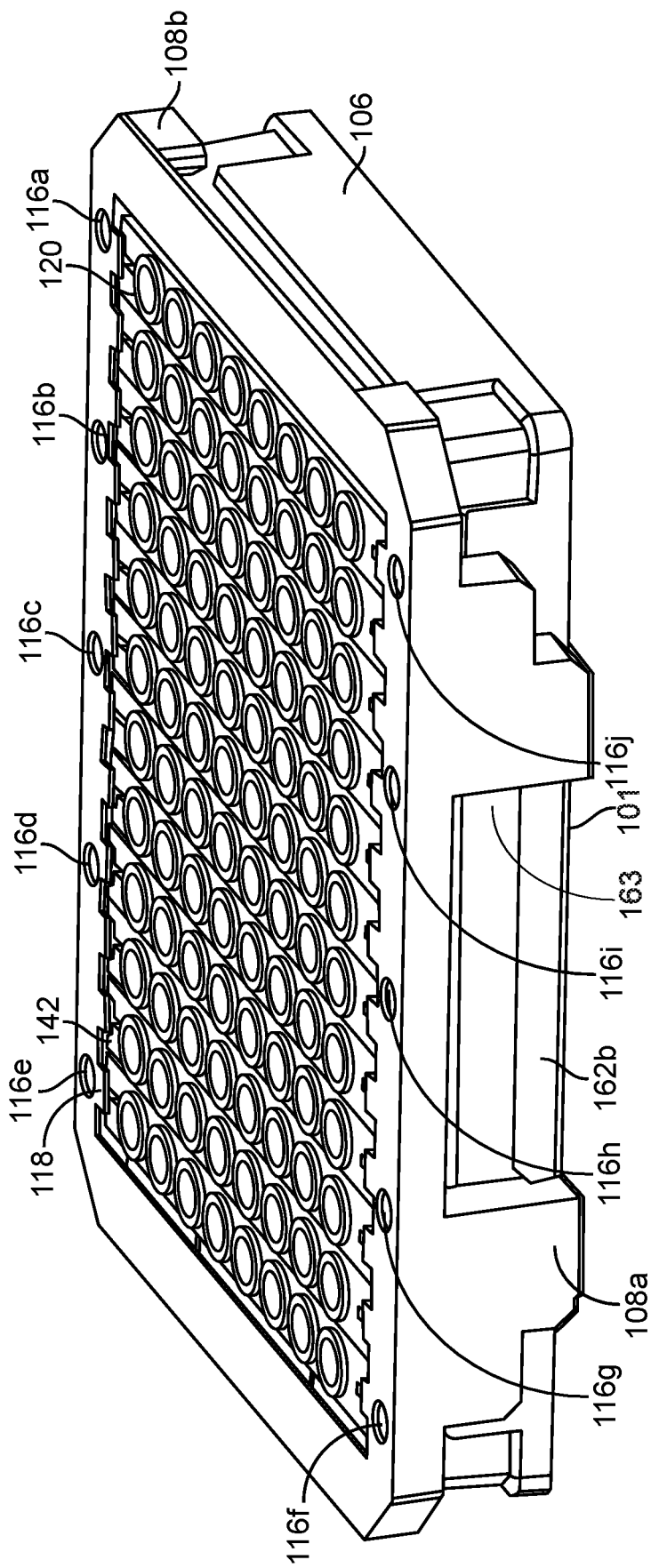

In another example, FIGS. 6A and 6B show a base plate 101 comprising a first tab 162a and a second tab 162b. FIG. 6A schematically illustrates the base plate 101 detached from the microplate 106. FIG. 6B schematically illustrates the base plate 101 attached or coupled with the microplate 106. The first tab 162a may extend from a first longitudinal side of the base plate 101 and a second tab 162b may extend from a second longitudinal side 163 of the base plate 101, as shown in FIGS. 6A and 6B. The first tab 162a and the second tab 162b may be configured to engage a first longitudinal side (not shown in FIGS. 6A and 6B) of the microplate and a second longitudinal side 163 of the microplate. The base plate 101 may comprise a first protrusion 164a, a second protrusion 164b, a third protrusion 164c, and a fourth protrusion 164d, as shown in FIGS. 6A and 7B. The base plate 101 may secure the microplate by resting adjacent to the distal surface of the aligner 140. The first protrusion 164a, the second protrusion 164b, the third protrusion 164c, and the fourth protrusion 164d of the base plate 101 may rest adjacent to the distal surface of the aligner 140 (e.g., to the third horizontal surface 148c and the fourth horizontal surface 148d of the aligner 140). The base plate 101 may secure the microplate by reversibly attaching to the distal surface of the aligner 140. The base plate 101 may secure the microplate 106 by irreversibly attaching to the distal surface of the aligner 140. The base plate 101 may reversibly attach to the distal surface of the aligner 140 by a magnetic force. For example, the base plate 101 may comprise an attraction unit (not shown in the figures) that reversibly attaches to the distal surface of the aligner 140. The base plate 101 may comprise a first attraction unit that reversibly attaches to a second attraction unit (not shown in the figures) located on the distal surface of the aligner 140. The attraction unit may be located on the proximal surface of the base plate 101. The attraction unit may be located on the proximal surface of the base plate 101. The base plate 101 may comprise a first magnet that reversibly attaches to a second magnet of opposite polarity (not shown in the figures) located on the distal surface of the aligner 140.

FIGS. 7A-7D schematically illustrate various views of the base plate 101. The base plate 101 may be a ferritic stainless steel material. The base plate 101 may be a ferromagnetic material. The ferromagnetic material may be copper, iron, ferric oxide, iron (II, III) oxide, manganese, nickel, yttrium iron garnet, chromium dioxide, gadolinium, terbium, dysprosium, trevorite, europium oxide, or a combination thereof. The ferromagnetic material may be cobalt, ferritic stainless steel, martensitic stainless steel, or a combination thereof. The base plate 101 may be a non-ferromagnetic metal. Non-limiting examples of the non-ferromagnetic metal include aluminum, aluminum alloys, copper, lead, nickel, tin, titanium, zinc, brass, and annealed austenitic stainless steel. The base plate 101 may be stainless steel AISI (American Iron and Steel Institute) 304. The base plate 101 may be stainless steel AISI (American Iron and Steel Institute) 302. The base plate 101 may be stainless steel AISI (American Iron and Steel Institute) 316 or 316L. The base plate 101 may be electropolished stainless steel.

The base plate 101 may have a length 170 (as shown in FIG. 7B) of about 10 cm. The base plate 101 may have a length 170 of at least about 5 cm to about 20 cm or more. The base plate 101 may have a length 170 of at least about 5 cm. The base plate 101 may have a length 170 of at most about 20 cm. The base plate 101 may have a length 170 of about 5 cm to about 10 cm, about 5 cm to about 15 cm, about 5 cm to about 20 cm, about 10 cm to about 15 cm, about 10 cm to about 20 cm, or about 15 cm to about 20 cm. The base plate 101 may have a length 170 of about 5 cm, about 10 cm, about 15 cm, or about 20 cm.

The base plate 101 may have a width 172 (as shown in FIG. 7B) of about 7.5 cm. The base plate 101 may have a width 172 of at least about 5 cm to about 15 cm or more. The base plate 101 may have a width 172 of at least about 5 cm. The base plate 101 may have a width 172 of at most about 15 cm. The base plate 101 may have a width 172 of about 5 cm to about 6 cm, about 5 cm to about 7 cm, about 5 cm to about 7.5 cm, about 5 cm to about 8 cm, about 5 cm to about 9 cm, about 5 cm to about 10 cm, about 5 cm to about 15 cm, about 6 cm to about 7 cm, about 6 cm to about 7.5 cm, about 6 cm to about 8 cm, about 6 cm to about 9 cm, about 6 cm to about 10 cm, about 6 cm to about 15 cm, about 7 cm to about 7.5 cm, about 7 cm to about 8 cm, about 7 cm to about 9 cm, about 7 cm to about 10 cm, about 7 cm to about 15 cm, about 7.5 cm to about 8 cm, about 7.5 cm to about 9 cm, about 7.5 cm to about 10 cm, about 7.5 cm to about 15 cm, about 8 cm to about 9 cm, about 8 cm to about 10 cm, about 8 cm to about 15 cm, about 9 cm to about 10 cm, about 9 cm to about 15 cm, or about 10 cm to about 15 cm. The base plate 101 may have a width 172 of about 5 cm, about 6 cm, about 7 cm, about 7.5 cm, about 8 cm, about 9 cm, about 10 cm, or about 15 cm.

The first tab 162a and the second tab 162b may have a length of about 4.9 cm. The first tab 162a and the second tab 162b may have a length of about 1 cm to about 15 cm. The first tab 162a and the second tab 162b may have a length of at least about 1 cm. The first tab 162a and the second tab 162b may have a length of at most about 15 cm. The first tab 162a and the second tab 162b may have a length of about 1 cm to about 2 cm, about 1 cm to about 3 cm, about 1 cm to about 4 cm, about 1 cm to about 5 cm, about 1 cm to about 6 cm, about 1 cm to about 7 cm, about 1 cm to about 8 cm, about 1 cm to about 9 cm, about 1 cm to about 10 cm, about 1 cm to about 15 cm, about 2 cm to about 3 cm, about 2 cm to about 4 cm, about 2 cm to about 5 cm, about 2 cm to about 6 cm, about 2 cm to about 7 cm, about 2 cm to about 8 cm, about 2 cm to about 9 cm, about 2 cm to about 10 cm, about 2 cm to about 15 cm, about 3 cm to about 4 cm, about 3 cm to about 5 cm, about 3 cm to about 6 cm, about 3 cm to about 7 cm, about 3 cm to about 8 cm, about 3 cm to about 9 cm, about 3 cm to about 10 cm, about 3 cm to about 15 cm, about 4 cm to about 5 cm, about 4 cm to about 6 cm, about 4 cm to about 7 cm, about 4 cm to about 8 cm, about 4 cm to about 9 cm, about 4 cm to about 10 cm, about 4 cm to about 15 cm, about 5 cm to about 6 cm, about 5 cm to about 7 cm, about 5 cm to about 8 cm, about 5 cm to about 9 cm, about 5 cm to about 10 cm, about 5 cm to about 15 cm, about 6 cm to about 7 cm, about 6 cm to about 8 cm, about 6 cm to about 9 cm, about 6 cm to about 10 cm, about 6 cm to about 15 cm, about 7 cm to about 8 cm, about 7 cm to about 9 cm, about 7 cm to about 10 cm, about 7 cm to about 15 cm, about 8 cm to about 9 cm, about 8 cm to about 10 cm, about 8 cm to about 15 cm, about 9 cm to about 10 cm, about 9 cm to about 15 cm, or about 10 cm to about 15 cm. The first tab 162a and the second tab 162b may have a length of about 1 cm, about 2 cm, about 3 cm, about 4 cm, about 5 cm, about 6 cm, about 7 cm, about 8 cm, about 9 cm, about 10 cm, or about 15 cm.

In another example, the microplate holder may comprise a frame, comprising projections and recesses. The frame may comprise four walls extending downwardly from each side of the frame. In other words, the frame may have a thickness that spans the height of the microplate creating a cover for the microplate. In another example, the microplate holder may comprise a frame comprising projections and recesses. The frame may comprise four walls extending downwardly from each side of the frame and a base plate that rests adjacent to the edges of the four walls. The base plate may be sized to match the dimensions of the frame and/or the microplate. The base plate may be permanently attached to the frame. The base plate may be irreversibly attached to the frame.

Microplate Holder Methods

In an aspect, the present disclosure provides a method of securing a microplate, comprising: attaching a microplate holder to the microplate, said microplate holder comprising: a base plate; an aligner configured to accept said microplate, wherein said aligner comprises a proximal surface, a distal surface, and an attraction unit between said proximal surface and said distal surface, which attraction unit is attractable towards said base plate to position said aligner adjacent to said base plate; and a frame configured to rest adjacent to said aligner and a proximal surface of said microplate, wherein said frame comprises a plurality of projections that extend along a direction parallel to said proximal surface of said aligner when said frame is positioned adjacent to said aligner.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

The following examples are provided for illustrative purposes. These examples are not intended to be limiting.

Example 1—Sealing of Tube Strips Using the Microplate Holder

In an example, a 96 well PCR microplate is used for the manipulation, processing, and/or preparation of reagents. The PCR microplate comprises twelve PCR, cap-less tube strips. Each PCR tube strip comprises a total of eight tubes. During the reagent manipulation, processing, and/or preparation process, a volume of a reagent is placed in each tube. The working volume of each tube in the tube strip is about 200 µl. The working volume of the reagent is verified during the reagent manipulation, processing, and/or preparation process. Then, the tube strips are sealed using an aluminum cover sheet with a polymer backing. The aluminum cover sheet is placed onto the top surface of the microplate (i.e., onto the opened tubes). The polymer backing faces the opening of the tubes. The tubes are heat sealed using a plate sealer. The laser device cuts the aluminum cover sheet and the plastic connecting each tube strip (i.e., in between each row of wells in the microplate). The microplate holder secures the microplate and the tube strips during the heat sealing step of the reagent manipulation, processing, and/or preparation. The microplate holder, specifically the projections of the frame, prevents warping of the tube strips during heat sealing. The recesses of the frame enable and provide enough space for the plate sealer device to seal each row of tube strips. The tube strips are sealed and preserve their original shape (i.e., the tube strips do not undergo any dimensional distortion during the heat sealing process when the microplate holder is used).

What is claimed is:

1. A microplate holder for securing a microplate comprising a proximal surface and a distal surface on opposite sides of the microplate, the microplate holder comprising:
   a base plate comprising a proximal surface and a distal surface on opposite sides of the base plate, wherein the distal surface of the microplate rests adjacent the proximal surface of the base plate;
   an aligner configured to accept the microplate, wherein the aligner comprises a proximal surface and a distal surface on opposite sides of the aligner and an attraction unit between the proximal surface and the distal surface of the aligner, wherein the attraction unit secures the distal surface of the aligner to the proximal surface of the base plate by magnetic force; and
   a frame configured to rest directly on top of and contact the proximal surface of the aligner and the proximal surface of the microplate, wherein the frame comprises a plurality of projections that extend along a direction parallel to the proximal surface of the aligner and over the proximal surface of the microplate when present;

wherein the base plate, the aligner, the frame, and the microplate are separable from each other.

2. The microplate holder of claim 1, wherein said base plate comprises an additional attraction unit that aligns with the attraction unit of the aligner.

3. The microplate holder of claim 2, wherein said additional attraction unit is a magnet.

4. The microplate holder of claim 1, wherein said base plate comprises one or more posts that are attractable towards said attraction unit.

5. The microplate holder of claim 4, wherein said one or more posts comprise an additional attraction unit.

6. The microplate holder of claim 5, wherein said additional attraction unit is a magnet.

7. The microplate holder of claim 4, wherein said one or more posts are configured to abut at least one edge of said microplate.

8. The microplate holder of claim 4, wherein said one or more posts restrict a lateral or longitudinal movement of said microplate.

9. The microplate holder of claim 1, wherein said base plate comprises a first tab extending from a first longitudinal side of said base plate and a second tab extending from a second longitudinal side of said base plate.

10. The microplate holder of claim 1, wherein the aligner comprises a lateral wall between the proximal and distal surfaces of the aligner, and a first arm extending from a first end of the lateral wall and a second arm extending from a second end of said lateral wall.

11. The microplate holder of claim 1, wherein said frame comprises at least one frame hole configured to align with at least one aligner hole.

12. The microplate holder of claim 11, wherein said at least one frame hole and said at least one aligner hole are configured to accept a screw or a securing pin.

13. The microplate holder of claim 12, wherein said screw or said securing pin anchors said frame and said aligner together.

14. The microplate holder of claim 1, wherein said frame comprises one or more snapping tabs extending from a side of said frame.

15. The microplate holder of claim 14, wherein said one or more snapping tabs makes a mechanical contact with one or more aligner snapping tab apertures.

16. The microplate holder of claim 1, wherein said frame comprises an additional attraction unit.

17. The microplate holder of claim 16, wherein said additional attraction unit is a magnet.

18. The microplate holder of claim 16, wherein said additional attraction unit is attractable towards said aligner to position said frame adjacent to said aligner and said proximal surface of said microplate.

19. The microplate holder of claim 1, wherein said microplate holder prevents or restricts movement of said microplate.

20. The microplate holder of claim 19, wherein said movement is a lateral movement, a longitudinal movement, or a proximal movement away from said base plate.

21. The microplate holder of claim 1, wherein the plurality of projections aligns with rows of wells in the microplate.

22. A method of securing a microplate comprising a proximal surface and a distal surface on opposite sides of the microplate, the method comprising: attaching a microplate holder to the microplate, the microplate holder comprising:
 a base plate comprising a proximal surface and a distal surface on opposite sides of the base plate, wherein the distal surface of the microplate rests adjacent the proximal surface of the base plate;
 an aligner configured to accept the microplate, wherein the aligner comprises a proximal surface and a distal surface on opposite sides of the aligner and an attraction unit between the proximal surface and the distal surface of the aligner, wherein the attraction unit secures the distal surface of the aligner to the proximal surface of the base plate by magnetic force; and
 a frame configured to rest directly on top of and contact the proximal surface of the aligner and the proximal surface of the microplate, wherein the frame comprises a plurality of projections that extend along a direction parallel to the proximal surface of the aligner and over the proximal surface of the microplate when present;
 wherein the base plate, the aligner, the frame, and the microplate are separable from each other.

* * * * *